(12) United States Patent
Veraitch et al.

(10) Patent No.: US 12,728,422 B2
(45) Date of Patent: Sep. 8, 2026

(54) DELIVERY CONSUMABLE FOR DELIVERING A FLUID TO A BIOREACTOR

(71) Applicant: Oribiotech LTD, London (GB)

(72) Inventors: Farlan Veraitch, London (GB); Richard Smith, Cambridgeshire (GB); Neil Litten, Reading (GB); William Raimes, London (GB)

(73) Assignee: ORIBIOTECH LTD., London (GB)

(*) Notice: Subject to any disclaimer, the term of this patent is extended or adjusted under 35 U.S.C. 154(b) by 777 days.

(21) Appl. No.: 17/905,991

(22) PCT Filed: Mar. 9, 2021

(86) PCT No.: PCT/GB2021/050577
§ 371 (c)(1),
(2) Date: Sep. 9, 2022

(87) PCT Pub. No.: WO2021/181077
PCT Pub. Date: Sep. 16, 2021

(65) Prior Publication Data

US 2023/0115386 A1 Apr. 13, 2023

(30) Foreign Application Priority Data

Mar. 9, 2020 (GB) ..................................... 2003403
Dec. 16, 2020 (GB) ..................................... 2019859

(51) Int. Cl.
*B01L 3/00* (2006.01)
*C12M 1/00* (2006.01)
(Continued)

(52) U.S. Cl.
CPC ................ *B01L 3/563* (2013.01); *B01L 3/52* (2013.01); *C12M 1/10* (2013.01); *C12M 1/268* (2013.01);
(Continued)

(58) Field of Classification Search
CPC .... B01L 3/563; B01L 3/52; B01L 2200/0689; B01L 2300/044; B01L 2300/123;
(Continued)

(56) References Cited

U.S. PATENT DOCUMENTS 2,847,996 A 8/1958 Cohen et al.
3,901,402 A 8/1975 Ayres
(Continued)

FOREIGN PATENT DOCUMENTS

EP 0711571 B1 12/1999
GB 2580356 A 7/2020
(Continued)

OTHER PUBLICATIONS

European Communication pursuant to Article 94(3) EPC for European Application No. 23178337.4, dated Oct. 23, 2024, 6 pages.
(Continued)

*Primary Examiner* — Samuel P Siefke
(74) *Attorney, Agent, or Firm* — TraskBritt

(57) ABSTRACT

The present disclosure provides a delivery consumable for delivering a fluid to a bioreactor. The delivery consumable comprises a container including a collapsible portion comprising a collapsible wall, and an intermediate portion connected to the collapsible portion and being adapted to hold a fluid. The deliver consumable also comprises a connector adapted to connect the intermediate portion to the bioreactor. The collapsible portion is adapted to collapse and urge the fluid through the connector and into the bioreactor.

17 Claims, 14 Drawing Sheets

(51) Int. Cl.

| | |
|---|---|
| ***C12M 1/10*** | (2006.01) |
| ***C12M 1/12*** | (2006.01) |
| ***C12M 1/26*** | (2006.01) |
| ***C12M 3/00*** | (2006.01) |

(52) U.S. Cl.

CPC ............ *C12M 23/34* (2013.01); *C12M 23/42* (2013.01); *C12M 23/46* (2013.01); *C12M 23/50* (2013.01); *C12M 29/00* (2013.01); *C12M 33/04* (2013.01); *C12M 37/04* (2013.01); *B01L 2200/0689* (2013.01); *B01L 2300/044* (2013.01); *B01L 2300/123* (2013.01); *B01L 2400/0478* (2013.01); *C12M 1/007* (2013.01); *C12M 23/26* (2013.01); *C12M 23/40* (2013.01)

(58) Field of Classification Search

CPC . B01L 2400/0478; C12M 1/10; C12M 1/268; C12M 23/34; C12M 23/42; C12M 23/46; C12M 23/50; C12M 29/00; C12M 33/04; C12M 37/04; C12M 1/007; C12M 23/26; C12M 23/40; C12M 3/00; C12M 23/28

See application file for complete search history.

(56) References Cited

U.S. PATENT DOCUMENTS

| | | | |
|---|---|---|---|
| 4,105,500 | A | 8/1978 | Libman et al. |
| 4,192,919 | A | 3/1980 | Raghavachari |
| 4,238,568 | A | 12/1980 | Lynn |
| 5,056,464 | A | 10/1991 | Lewis |
| 5,164,796 | A | 11/1992 | Di Guiseppi et al. |
| 5,652,143 | A | 7/1997 | Gombrich et al. |
| 5,658,531 | A | 8/1997 | Cope et al. |
| 5,761,885 | A | 6/1998 | Hansen |
| 6,432,697 | B1 | 8/2002 | Tice et al. |
| 6,716,187 | B1 | 4/2004 | Jorgensen et al. |
| 8,268,263 | B2 | 9/2012 | Campbell et al. |
| 8,415,144 | B2 | 4/2013 | Wilson et al. |
| 9,145,581 | B1 | 9/2015 | Lai |
| 9,180,252 | B2 | 11/2015 | Gelblum et al. |
| 9,380,973 | B2 | 7/2016 | Fletcher et al. |
| 2002/0025547 | A1 | 2/2002 | Rao |
| 2003/0060749 | A1 | 3/2003 | Aneas |
| 2003/0143727 | A1 | 7/2003 | Chang |
| 2006/0178644 | A1 | 8/2006 | Reynolds |
| 2007/0224676 | A1 | 9/2007 | Haq |
| 2007/0254356 | A1 | 11/2007 | Wilson et al. |
| 2008/0311650 | A1 | 12/2008 | Jakob et al. |
| 2009/0191620 | A1 | 7/2009 | Martin et al. |
| 2010/0077843 | A1 | 4/2010 | Doraisamy et al. |
| 2010/0083774 | A1 | 4/2010 | Schmiedl |
| 2010/0093551 | A1 | 4/2010 | Montagu |
| 2011/0076756 | A1 | 3/2011 | Wright |
| 2012/0083029 | A1 | 4/2012 | Tsumura et al. |
| 2012/0123297 | A1 | 5/2012 | Brancazio |
| 2012/0202193 | A1 | 8/2012 | Heinrich |
| 2013/0029324 | A1 | 1/2013 | Rajagopal et al. |
| 2013/0281940 | A1 | 10/2013 | Gelblum et al. |
| 2014/0010740 | A1 | 1/2014 | Anitua Aldecoa |
| 2014/0048556 | A1 | 2/2014 | Pearcy et al. |
| 2014/0076454 | A1 | 3/2014 | Kjar |
| 2014/0170644 | A1 | 6/2014 | Hadayer et al. |
| 2015/0083320 | A1 | 3/2015 | Putnam |
| 2015/0151035 | A1 | 6/2015 | Huemer |
| 2015/0173660 | A1 | 6/2015 | Choon Meng |
| 2015/0252317 | A1 | 9/2015 | Lipkens et al. |
| 2015/0368602 | A1 | 12/2015 | Galliher et al. |
| 2016/0152935 | A1 | 6/2016 | Roosloot et al. |
| 2016/0265022 | A1 | 9/2016 | Yang-Woytowitz et al. |
| 2016/0279551 | A1 | 9/2016 | Foucault |
| 2018/0257051 | A1 | 9/2018 | De et al. |
| 2018/0362910 | A1 | 12/2018 | Bores et al. |
| 2019/0030527 | A1 | 1/2019 | Walsh et al. |
| 2019/0046977 | A1 | 2/2019 | Ronsick et al. |
| 2019/0062681 | A1 | 2/2019 | Fan et al. |
| 2020/0123493 | A1 | 4/2020 | Schndube et al. |
| 2020/0190457 | A1 | 6/2020 | Veraitch et al. |
| 2022/0154245 | A1 | 5/2022 | Ishimaru et al. |

FOREIGN PATENT DOCUMENTS

| | | | |
|---|---|---|---|
| GB | 2590523 | B | 12/2021 |
| JP | 63-503201 | A | 11/1988 |
| JP | 2008-237203 | A | 10/2008 |
| JP | 2020-054392 | A | 4/2020 |
| WO | 87/02252 | A1 | 4/1987 |
| WO | 87/06952 | A1 | 11/1987 |
| WO | 2008/068502 | A1 | 6/2008 |
| WO | 2009/032645 | A1 | 3/2009 |
| WO | 2009/093995 | A1 | 7/2009 |
| WO | 2010/024906 | A1 | 3/2010 |
| WO | 2011/144561 | A1 | 11/2011 |
| WO | 2013/036429 | A2 | 3/2013 |
| WO | 2015/187518 | A1 | 12/2015 |
| WO | 2016/185221 | A1 | 11/2016 |
| WO | 2018/015561 | A1 | 1/2018 |
| WO | 2018/087558 | A1 | 5/2018 |
| WO | 2019/199406 | A1 | 10/2019 |
| WO | 2021/123760 | A1 | 12/2020 |
| WO | 2021/123762 | A1 | 6/2021 |

OTHER PUBLICATIONS

European Search Report Opinion for European Application No. 23178337.4, dated Oct. 2, 2023, 4 pages.

International Search Report for International Application No. PCT/GB2021/050577, mailed Jun. 9, 2021, 4 pages.

International Written Opinion for International Application No. PCT/GB2021/050577, mailed Jun. 9, 2021, 6 pages.

United Kingdom Patent Examination Report for United Kingdom Patent Application No. GB2019859.4 , dated Nov. 26, 2021, 3 pages.

United Kingdom Patent Examination Report for United Kingdom Patent Application No. GB2103240.4 , dated Feb. 17, 2022, 3 pages.

United Kingdom Search Report for United Kingdom Patent Application No. GB2019859.4, dated Jun. 10, 2021, 3 pages.

United Kingdom Search Report for United Kingdom Patent Application No. GB2103240.4, dated Aug. 20, 2021, 3 pages.

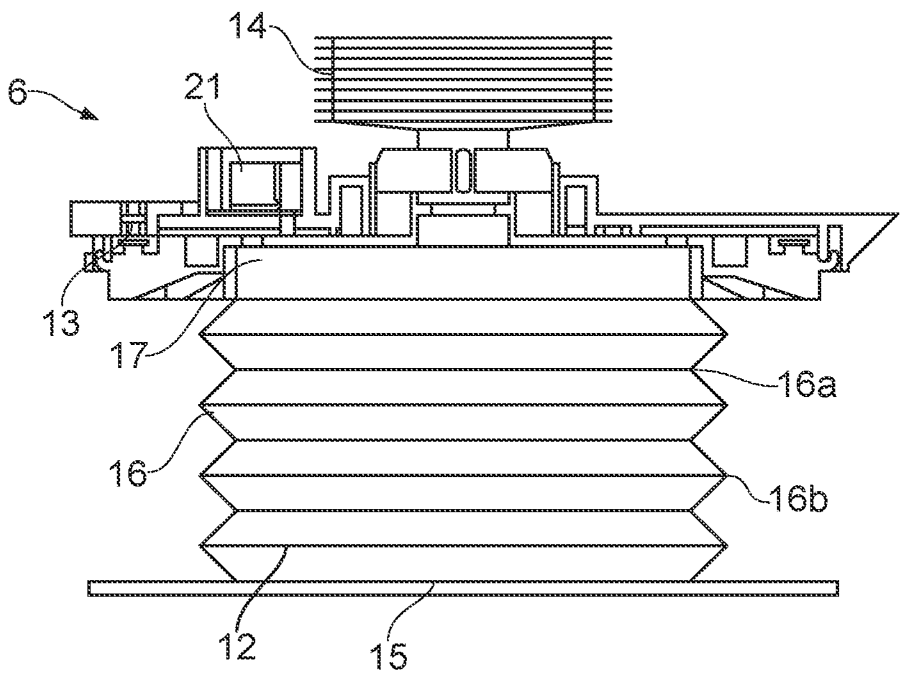
FIG. 3
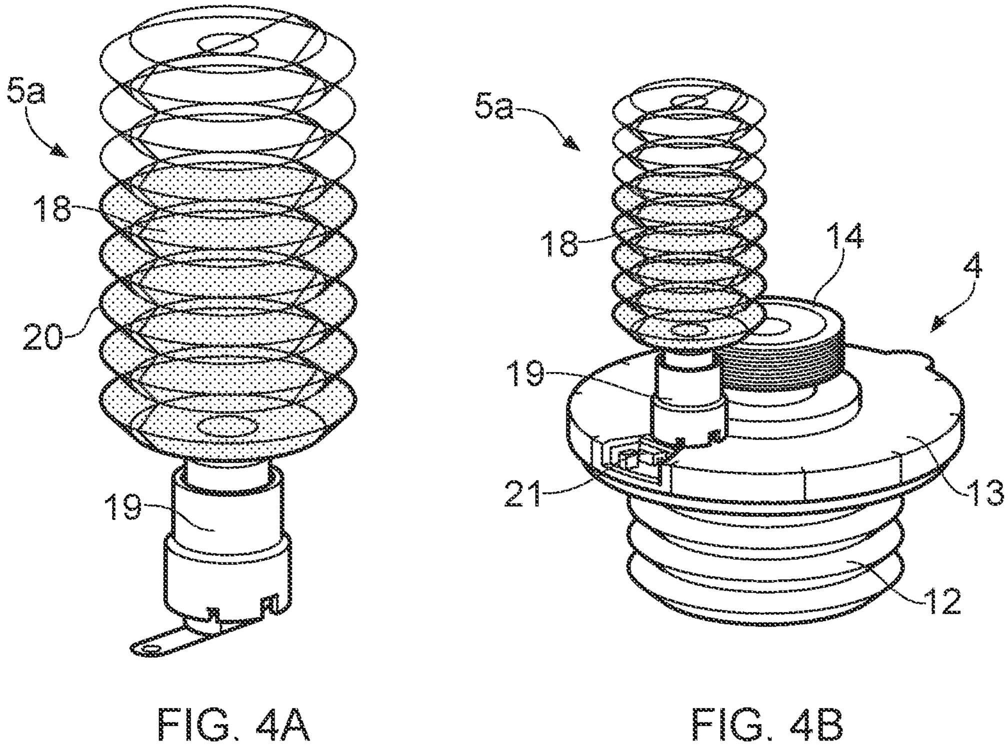
FIG. 4A
FIG. 4B

DELIVERY CONSUMABLE FOR DELIVERING A FLUID TO A BIOREACTOR

CROSS-REFERENCE TO RELATED APPLICATIONS

This application is a national phase entry under 35 U.S.C. § 371 of International Patent Application PCT/GB2021/050577, entitled "DELIVERY CONSUMABLE FOR DELIVERING A FLUID TO A BIOREACTOR," filed Mar. 9, 2021, designating the United States of America and published as International Patent Publication WO 2021/181077 A1 on Sep. 16, 2021, which claims the benefit under Article 8 of the Patent Cooperation Treaty to Great Britain Patent Application Serial Nos. 2003403.9, filed Mar. 9, 2020, and 2019859.4, filed Dec. 16, 2020.

TECHNICAL FIELD

This disclosure relates to a delivery consumable for delivering a fluid to a bioreactor. The bioreactor is suitable for performing one or more unit operations in a cell processing method, for example, in cell and/or gene therapy manufacturing processing. The fluid delivery consumable is operable to transfer a fluid from the fluid delivery consumable to the bioreactor.

BACKGROUND

Cell and gene therapy manufacturing processes are often complex and include manual or semi-automated steps across several devices. Equipment systems used in various steps, or unit operations, of cell-based therapeutic products (CTP) manufacturing may include devices for various functions. These various functions may be, for example, cell collection, cell isolation, cell selection, cell expansion, cell washing, volume reduction, cell storage or transportation. The unit operations can vary immensely based on the manufacturing model (i.e., autologous versus allogenic), cell type, intended purpose, among other factors. In addition, cells are "living" entities sensitive to even the simplest manipulations, for example, such as differences in a cell transferring procedure. The role of cell manufacturing equipment in ensuring scalability and reproducibility is an important factor for cell and gene therapy manufacturing.

In addition, cell-based therapeutic products (CTP) have gained significant momentum thus there is a need for improved cell manufacturing equipment for various cell manufacturing procedures. These manufacturing procedures, may include, for example, stem cell enrichment, generation of chimeric antigen receptor (CAR) T cells, and various cell manufacturing processes such as collection, purification, gene modification, incubation, recovery, washing, infusion into a patient, or freezing.

The culture or processing of cells typically requires the use of a device to hold the cells, for example, in an appropriate culture medium when culturing the cells. The known devices include shaker flasks, roller bottles, T-flasks, bags and the like. Such devices are typically required to be connected to other devices, such as containers, interfaces or the like, so that various media may be introduced to, or removed from, the device holding the cells. Typically, cells in a culture medium can be added to the device from a flexible bag that is attached using a connecting tube. Alternatively, cells can be transferred by a pipette or by a syringe.

The production of autologous CAR T cells is carried out by a variety of manufacturing approaches all comprising the same common steps. First, the patient's white blood cells (WBCs) are isolated by leukapheresis and washed. Then, the T cells are activated, transduced with the CAR transgene, expanded to the required cell numbers for therapy, formulated and filled. After quality control testing and preparatory lymphodepleting chemotherapy for the patient, the product is injected into the patient.

BRIEF SUMMARY

In accordance with the present disclosure there is provided a delivery consumable for delivering a fluid to a bioreactor, the delivery consumable comprising:

- a container having:
  - a collapsible portion comprising a collapsible wall; and
  - an intermediate portion connected to the collapsible portion and being adapted to hold a fluid, and
- a connector for connecting the intermediate portion to the bioreactor,
- wherein during use the collapsible portion is collapsible so as to urge the fluid through the connector and into the bioreactor.

In examples, the collapsible portion may comprise a frustrum-shaped collapsible wall extending from a first end at the intermediate portion to a second end of the collapsible portion opposite to the first end, the first end being larger than the second end. The frustrum-shaped collapsible wall may be a frustoconical collapsible wall. In examples, the second end of the frustrum-shaped collapsible wall is connected to the intermediate portion.

In examples, the second end of the collapsible portion may comprise a cap.

In examples, the collapsible portion may further comprise a second frustrum-shaped collapsible wall extending from a second end to a first end, the first end being larger than the second end, and wherein the second end of the second frustrum-shaped collapsible wall is joined to the second end of the frustrum-shaped collapsible wall. The second frustrum-shaped collapsible wall may be a second frustoconical collapsible wall. In examples, the first end of second frustrum-shaped collapsible wall may comprise a cap.

In examples, the collapsible portion may be configured to hold at least a part of the fluid.

In examples, the delivery consumable may further comprising a divider between the intermediate portion and the collapsible portion. The divider may comprise a valve. In examples, the intermediate portion may be configured to hold the entire fluid provided to the delivery consumable. In examples, the valve may be a two-way valve.

In examples, the collapsible wall may comprise a bellows wall. In examples, the bellows wall may comprise a plurality of inward folds and a plurality of outward folds arranged alternately between opposing ends of the collapsible wall.

In examples, the collapsible wall may comprise a silicone or a thermoelastic polymer, for example, a polyvinyl chloride. In other examples, the collapsible wall may comprise a low density polyethylene. In examples, a surface of the collapsible wall may comprise a coating, for example, an outer surface of the collapsible wall may comprise a coating. Additionally or alternatively, an inner surface of the collapsible wall may comprise a coating. In examples, the coating is gas-impermeable.

In examples, the connector comprises a seal arranged to seal an end of the intermediate portion. The connector may be actuatable to open or break the seal and create a fluid connection from the intermediate portion through the connector. In examples, the connector may comprise a needle actuatable to pierce the seal. In examples, the seal may comprise a septum seal.

In examples, the delivery consumable may further comprise a feed tube in fluid communication with the intermediate portion. In examples, the intermediate portion may comprise an external spigot for attachment of the feed tube. In examples, the feed tube may be closable, for example, crimpable or weldable, so as to seal the feed tube after a fluid has been added to the delivery consumable.

In examples, the delivery consumable may be a cell delivery consumable and the fluid may be a cell suspension. In examples, the delivery consumable may be a media delivery consumable and the fluid may be a medium, for example, a cell culturing medium.

In examples, the delivery consumable further comprises a fluid in the container, for example, a cell suspension or a medium.

In accordance with the present disclosure there is provided a method of delivering a fluid to a bioreactor, the method comprising: filling the delivery consumable described above with a fluid, connecting the delivery consumable to the bioreactor via the connector of the delivery consumable; and at least partially collapsing the collapsible portion of the delivery consumable to transfer the fluid into the bioreactor.

BRIEF DESCRIPTION OF THE DRAWINGS

Embodiments of the disclosure are further described hereinafter with reference to the accompanying drawings, in which:

FIG. 3 illustrates the bioreactor;

FIGS. 4A and 4B show an example of a fluid delivery consumable attaching to the bioreactor;

DETAILED DESCRIPTION

Figure 1:
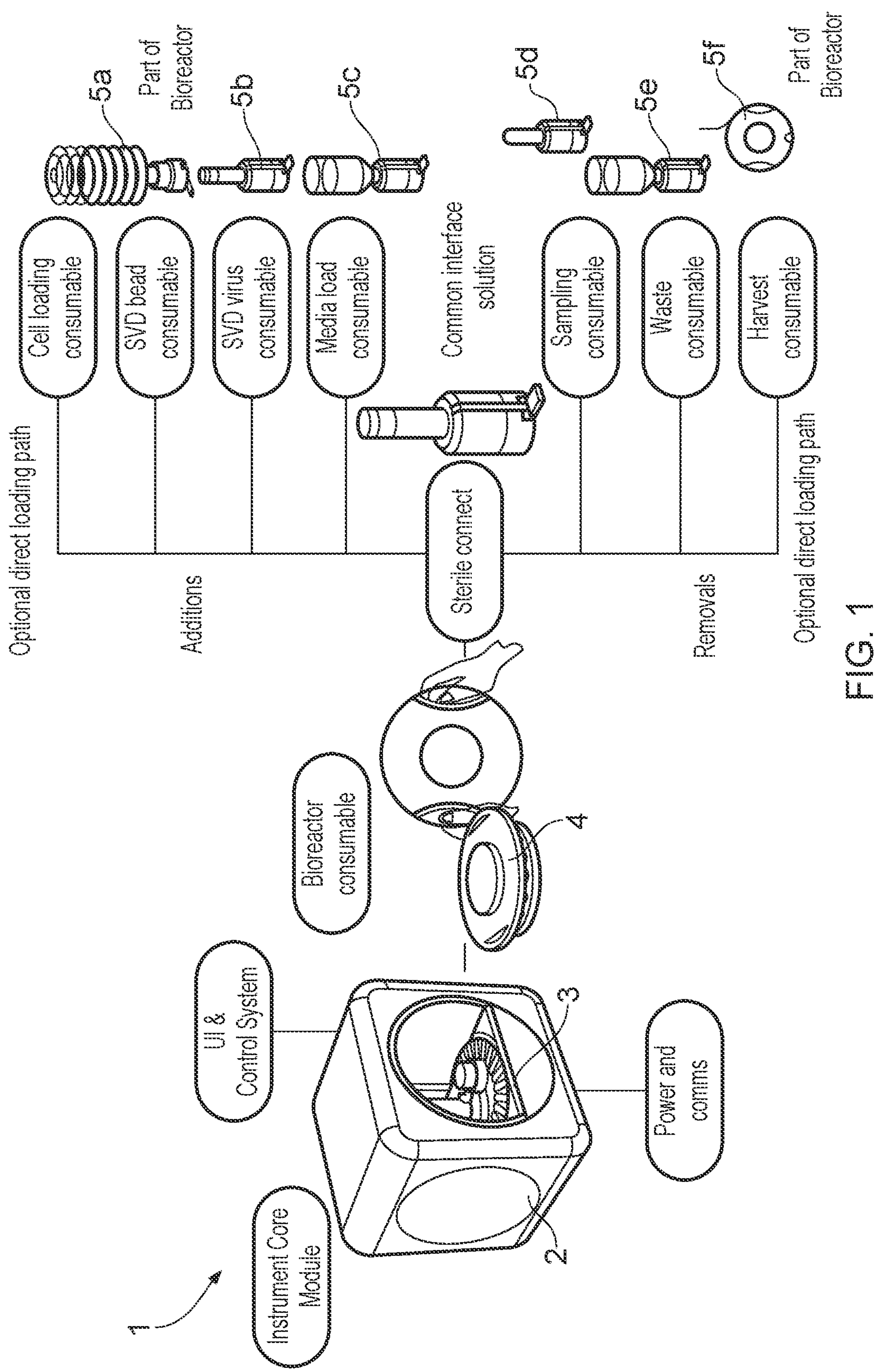
FIG. 1 shows a cell processing system that includes a bioreactor.

FIG. 1 shows a cell processing system 1 that includes a cell processing housing 2, a cell processing platform 3, a bioreactor 4, and various accessories, for example, "consumables" 5*a*-5*f*.

The cell processing housing 2 provides a closed environment for the cell processing platform 3 and is provided with power, connectivity and other utilities needed for the cell processing as described hereinafter. The cell processing platform 3 is adapted to receive the bioreactor 4 and support the bioreactor 4 within the cell processing housing 2. The cell processing platform 3 may include various components and systems that interact with the bioreactor 4 and/or the consumables 5*a*-5*f*. For example, the cell processing platform 3 may include an agitator that acts to agitate the bioreactor 4 so as to agitate a cell suspension provided within the bioreactor 4. In other examples, the cell processing platform 3 may include an accessory support arm adapted to hold one or more consumables 5*a*-5*f*. In examples, the cell processing platform 3 may include an actuator operable to actuate one or more the consumables 5*a*-5*f*. The cell processing platform 3 may be configured for automated operation of the cell processing system 1, or may permit manual operation.

The bioreactor 4, described in more detail with reference to FIG. 3, includes a container 12 and an interface plate 13. During use the container 12 holds a fluid in which the cell processing occurs. In particular, the fluid comprises a population of cells present in a liquid medium. The container 12 may be expandable, for example, by having a bellows wall. The bioreactor 4 is held in the cell processing housing 2 such that the container 12 can expand and retract as it is filled and emptied. The interface plate 13 may be engaged by the cell processing platform 3 and provides various functions relating to the bioreactor 4. For example, the interface plate 13 may have one or more connectors for transfer of fluids into and out of the container 12.

The consumables 5*a*-5*f* are for connecting to the bioreactor 4, optionally via the cell processing platform 3, in order to facilitate process steps of the cell culturing process.

In examples, a cell delivery consumable 5*a* is provided. The cell delivery consumable 5*a* is adapted to connect to the bioreactor 4 and deliver a cell suspension to the bioreactor 4. In particular, the cell delivery consumable 5*a* has a container that is filled with a cell suspension, and a connector that connects to the bioreactor 4 (optionally via the cell processing platform 3). The cell delivery consumable 5*a* is operable to transfer the cell suspension from the cell delivery consumable 5*a* into the bioreactor 4. The cell suspension may include "live" cells and a medium. Accordingly, the cell delivery consumable 5*a* delivers the cell suspension to a bioreactor 4.

The population of cells may comprise any cell type. Suitably the population of cells may comprise a homogenous population of cells. Alternatively, the population of cells may comprise a mixed population of cells.

The population of cells may comprise any human or animal cell type, for example: any type of adult stem cell or primary cell, T cells, CAR-T cells, monocytes, leukocytes, erythrocytes, NK cells, gamma delta t cells, tumor infiltrating t cells, mesenchymal stem cells, embryonic stem cells, induced pluripotent stem cells, adipose derived stem cells, Chinese hamster ovary cells, NS0 mouse myeloma cells, HELA cells, fibroblasts, HEK cells, insect cells, organoids, etc. Suitably the population of cells may comprise T-cells.

Alternatively, the population of cells may comprise any microorganism cell type, for example: bacterial, fungal, Archaean, protozoan, algal cells.

In examples, a bead loading consumable 5*b* is provided. The bead loading consumable 5*b* may hold a bead suspension, for example, a suspension of magnetic beads in water. The bead loading consumable 5*b* is operable to deliver the beads to the bioreactor 4. The magnetic beads may be used in a cell selection process.

In examples, the bead loading consumable 5*b* may alternatively or additionally be a virus loading consumable 5*b*.

The virus loading consumable **5*b* may hold a virus solution or suspension for delivery to the bioreactor 4**.

In examples, a media delivery consumable **5*c* may be provided. The media delivery consumable 5*c* may comprise a container that is filled with one or more media, for example, a cell culturing medium, and a connector that connects to the bioreactor 4. The media delivery consumable 5*c* is operable to move the medium into the bioreactor. In examples, the media delivery consumable 5*c* is collapsible, similar to the cell delivery consumable 5*a***. The medium may be a liquid.

In examples, the liquid medium may be any sterile liquid capable of maintaining cells. The liquid medium may be selected from: saline or may be a cell culture medium. The liquid medium may be a cell culture medium selected from any suitable medium, for example: DMEM, XVIVO 15, TexMACS. The liquid medium may be appropriate for the type of cells present in the population. For example, the population of cells comprises T cells and the liquid medium comprises XVIVO 10.

In examples, the liquid medium may further comprise additives, for example: growth factors, nutrients, buffers, minerals, stimulants, stabilizers or the like.

In examples, the liquid medium comprises growth factors such as cytokines and/or chemokines. The growth factors may be appropriate for the type of cells present in the population and the desired process to be carried out. The liquid medium may comprise stimulants such as antigens or antibodies, which may be mounted on a support. Suitable stimulants are appropriate for the type of cells present in the population and the desired process to be carried out. When culturing T-cells, for example, antibodies are provided as a stimulant in the liquid medium. The antibodies may be mounted on an inert support such as beads, for example: dynabeads.

The additives may be present in the liquid medium at an effective concentration. An effective concentration can be determined by the skilled person on the basis of the population of cells and the desired process to be carried out using known teachings and techniques in the art.

In examples, the population of cells are seeded in the liquid medium at a concentration of between 1×104 cfu/ml up to 1×108 cfu/ml.

In examples, a sampling consumable **5*d* may be provided. The sampling consumable 5*d* may comprise a sampling vial. In examples, the sampling consumable 5*d*** may comprise a vacutainer.

In examples, a waste consumable **5*e* may be provided. The waste consumable 5*e* may comprise a container, for example, an expandable container, adapted to receive a waste material removed from the bioreactor 4. The waste consumable 5*e*** may include a filter arranged to filter the cells and/or other media from the fluid within the bioreactor so as only to extract the waste components.

In examples, a cell harvesting consumable **5*f* may be provided. The cell harvesting consumable 5*f* may comprise a container, for example, an expandable container, adapted to receive the cells (and optionally a cell medium) at or toward the end of the cell culturing process. The cell harvesting consumable 5*f*** may include a filter arranged to filter a waste component from the cells and/or other media within the bioreactor so as only to extract the cells and desired media.

In examples, each of the consumables **5*a*-5*f* is connectable to the bioreactor 4 by a common connector. The connector may be that described in patent application PCT/GB2020/053229, as described further with reference to FIG. 5**.

The connector can be connected to the consumable **5*a*-5*f*, or may be an integral part of the consumable 5*a*-5*f*. Operation of the connector, for example, by twisting or sliding, moves a needle so as to create a fluid connection between each end of the connector. Accordingly, the connector allows each consumable 5*a*-5*f* to be connected to the bioreactor 4, and then actuation of the connector forms a fluid connection between the consumable 5*a*-5*f* and the bioreactor 4 for transfer of materials as set out above. As explained further below, the connectors ensures sterility of the bioreactor 4 and the consumable 5** while creating a fluid connection between the two.

Figure 2:
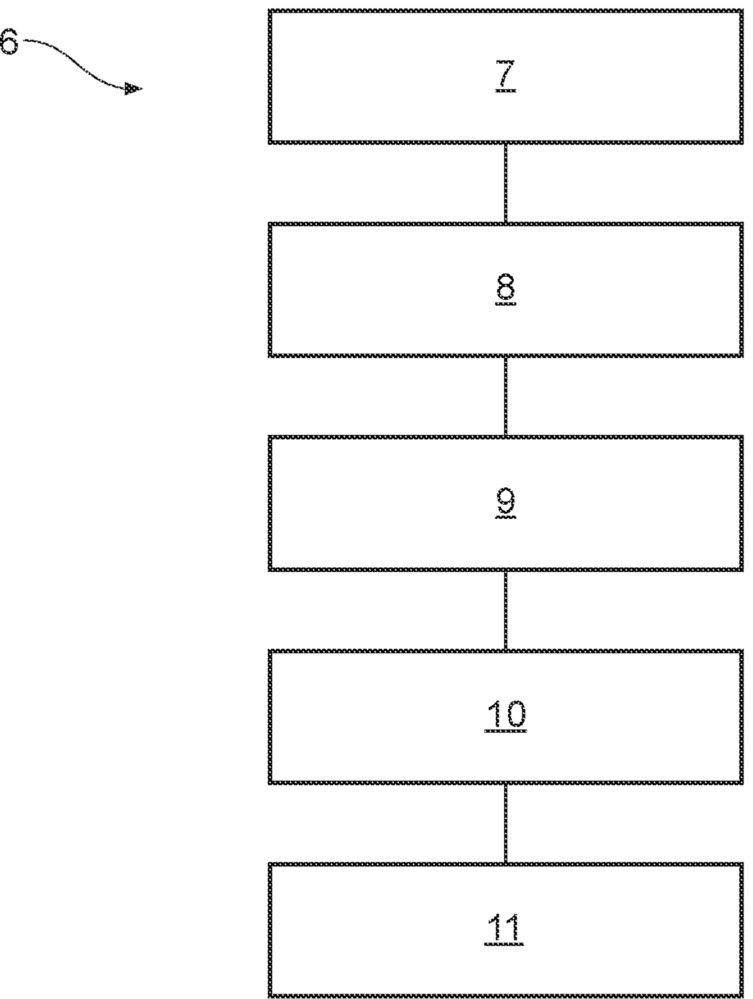
FIG. 2 schematically illustrates a cell culturing process.

FIG. 2 schematically illustrates a cell culturing process 6 based on the cell processing system 1 described with reference to FIG. 1. As shown in FIG. 2, initially the consumables **5*a*-5*f* are prepared at step 7. For example, a cell delivery consumable 5*a* may be filled with a cell suspension, and a virus loading consumable 5*b* may be filled with a virus suspension. A connector may be attached to the consumable 5*a*-5*f* before or after preparation. Preparation of the consumable(s) 5*a*-5*f* may include unpackaging the consumable (s) 5*a*-5*f* from a sterile package. It will be appreciated that only the consumables 5*a*-5*f* needed for the particular process, and the particular stage of the process, are prepared. For example, some processes would not use beads so a bead loading consumable 5*b* is not needed, and the cell harvesting consumable 5*f* is only needed at the end of the process 6**.

Next, cells are loaded into the bioreactor 4 at step 8. In particular, a cell delivery consumable **5*a* is connected to the bioreactor 4 and operated to transfer a cell suspension from the cell delivery consumable 5*a* into the bioreactor 4. The cell delivery consumable 5*a* is connected to the bioreactor 4 via a connector, as described above, which forms a fluid connection between the cell delivery consumable 5*a* and the bioreactor 4**.

Either before or after loading cells into the bioreactor 4 (step 8), the bioreactor 4 is loaded into the cell processing housing 2 at step 9. In some examples, the bioreactor 4 is attached to the cell processing platform 3 within the cell processing housing 2.

Within the cell processing housing 2 the cells are processed at step 10 in the bioreactor 4. During processing (step 10) the pressure, temperature, pH and other environmental characteristics within the bioreactor 4 are controlled to ensure that conditions enable cell processing. Cell processing (step 10) may comprise reprogramming the cells, for example, by using CAR-coding viral DNA. Cell processing (step 10) may comprise cell culturing.

During cell processing (step 10) additional consumables **5*a*-5*f* may be used to add materials to the bioreactor 4, to extract a sample from the bioreactor 4, and/or to extract waste from the bioreactor 4. For example, a bead loading consumable 5*b* may be used to add magnetic beads to the bioreactor. In examples, a virus loading consumable 5*b* may be used to add a virus suspension or solution to the bioreactor (e.g., CAR-coding viral DNA). In examples, a media delivery consumable 5*c* may be used to add one or more media to the bioreactor 4. For example, a media delivery consumable 5*c* may be used to add a balanced salt solution or a basal media to the bioreactor 4. In examples, a sampling consumable 5*d* may be used to extract a sample from the bioreactor for testing. In examples, during or after cell processing (step 10) a waste consumable 5*e* may be used to extract a waste media from the bioreactor 4**.

After cell processing (step 10) the cells are harvested at step 11. Cell harvesting (step 11) may initially use a waste consumable 5*e* to extract a waste component. A harvesting consumable 5*f* can be attached to bioreactor 4 to receive the cells from the bioreactor 4. The cells may be harvested in a media, for example, a cell suspension may be harvested.

As shown in FIG. 3, the bioreactor 4 comprises a container 12 and an interface plate 13. The interface plate 13 comprises at least one connector interface 21 for connecting to an external component, for example, one of the consumables 5*a*-5*f* described above. In examples, the connector interface 21 includes a septum seal that maintains a sealed environment within the container 12 and also permits a needle to pass through to create a fluid connection into the container 12.

The container 12 is a collapsible container. In particular, the container 12 has a bottom wall 15 disposed opposite to the interface plate 13, and a collapsible wall 16 defining a sidewall of the container 12. A top part 17 of the collapsible wall 16 is attached to the interface plate 13. The top part 17 may include a rigid ring or similar for attaching to the interface plate 13. The collapsible wall 16 is collapsible such that the bottom wall 15 can move toward and away from the interface plate 13, changing the internal volume of the container 12.

The collapsible wall 23 may be a bellows wall, having a concertina arrangement that allows the collapsible wall 23 to fold onto itself in order to collapse. In particular, the collapsible wall 23 may comprise a series of alternately arranged inward folds 16*a* and outward folds 16*b* that allow the collapsible wall 23 to collapse like a bellows or concertina. The inward folds 16*a* and outward folds 16*b* may be formed by thinned sections in the collapsible wall 23, with the inward folds 16*a* comprise a thinned section arranged on the outer surface of the collapsible wall 23, and the outward folds 16*b* comprising a thinned section arranged on the inner surface of the collapsible wall 23.

In other examples, the container 12 may be formed by sealed and telescopically arranged rings permitting the container 12 to elongate and shorten to change an internal volume of the container 12. In other examples, the container 12 may be made from a flexible or extendible material, for example, a resiliently flexible material, allowing the container 12 to expand and contract.

The container 12 can therefore expand and contract, or be expanded and contracted, according to the material held in the container 12 and/or an external force. In particular, the collapsible container 12 may expand as the cell culture within the container 12 grows, and/or as additional materials are added. The cell processing housing (2, see FIG. 1) may comprise an actuator adapted to move, for example, push and/or pull, the bottom wall 15 of the container 12 and/or the interface plate 13 to change the volume of the container 12.

As illustrated, the interface plate 13 also includes an expansion container 14, otherwise called a breathing container. The expansion container 14 allows for the container 12 to expand and contract without greatly changing the pressure in the container 12. Alternatively or additionally, the expansion container 14 may be operable, for example, by being mechanically or manually compressed or expanded, to expand or retract the collapsible wall 16 of the container 12 and thereby change a volume of the container 12. Alternatively or additionally, the expansion container 14 may be operable, for example, by being mechanically or manually compressed or expanded, to alter the pressure within the container 12.

FIGS. 4A and 4B illustrate an example of connecting a consumable to the bioreactor 4 of FIG. 3, for example, a cell delivery consumable 5*a* or a media delivery consumable 5*c*.

As shown, the consumable 5*a*, 5*c* has a container 18 and a connector 19. The container 18 comprises a collapsible wall 20. The collapsible wall 20 may be similar to the collapsible wall 16 of the container 12 of the bioreactor 4 illustrated in FIG. 3. In particular, the collapsible wall 20 comprises a series of alternating inward and outward folds that allow the collapsible wall 20 to collapse. The container 18 is filled with a fluid, for example, a cell suspension or cell culturing media, which has expanded the collapsible wall 20 to an extended state, as illustrated. In some examples, the container 18 comprises the connector 19, and in other examples the container 18 is attached to the connector 19, for example, by a threaded connection as illustrated further in FIG. 5.

As shown in FIG. 4B, the connector 19 is connected to the interface plate 13 of the bioreactor 4, in particular, to a connector interface 21 of the interface plate 13. In examples, the connector interface 21 comprises a seal, for example, a septum seal, that seals the bioreactor 4. The connector 19 is actuatable, as described with reference to FIG. 5, to form a fluid connection between the container 18 of the consumable 5*a*, 5*b* and the container 12 of the bioreactor 4. In examples, the connector 19 comprises a needle that is moved when the connector 19 is actuated in order to pierce the seal of the connector interface 21 and form a fluid connection with the bioreactor.

Once the fluid connection is established the fluid is transferred from the container 18 of the consumable 5*a*, 5*b* to the container 12 of the bioreactor 4. The fluid may be transferred by gravity. In particular, gravity will act to compress the container 18 by folding the collapsible wall 20, thereby urging the fluid through the fluid connection. Alternatively or additionally, the container 18 of the consumable 5*a*, 5*b* may be compressed, either manually by an operator or by an actuator of the cell processing system (1, see FIG. 1). Compressing the container 18 of the consumable 5*a*, 5*c* urges the fluid through the fluid connection and into the container 12 of the bioreactor 4.

Once the fluid has been transferred from the consumable 5*a*, 5*c* to the bioreactor 4 the consumable 5*a*, 5*c* can be detached from the bioreactor 4. On detaching the connector 19 from the connector interface 21 the seal of the connector interface 21 may reseal the connector interface 21. For example, the seal of the connector interface 21 may be a septum seal that reseals on withdrawal of the needle.

Figure 5:
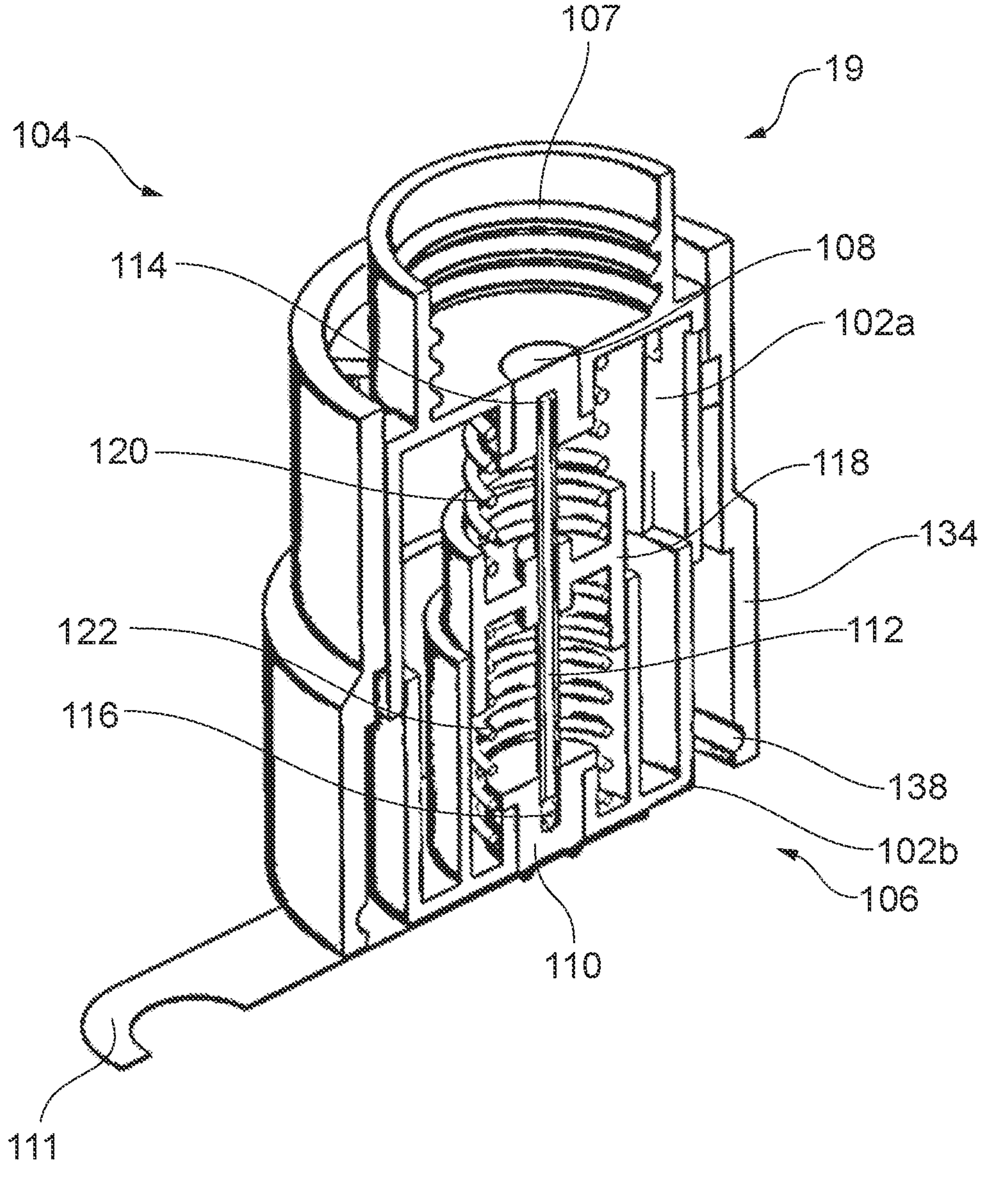
FIG. 5 shows an example connector for connecting the fluid delivery consumable to the bioreactor.

FIG. 5 illustrates the connector 19. The connector 19 is used to attach a consumable 5*a*-5*f* to the bioreactor 4, in particular, to the connector interface 21 of the interface plate 13 of the bioreactor 4. The connector 19 may be as described in patent application PCT/GB2020/053229.

In particular, as shown in FIG. 5 the connector 19 comprises a housing 102 having an upper housing portion 102*a* and a lower housing portion 102*b*. The housing 102 extends along a longitudinal axis between a distal end 104 and a proximal end 106. The upper housing portion 102*a* may be axially moveable, or slidable, with respect to the lower housing portion 102*b*, as will be described further below.

The housing 102 includes a threaded portion 107 at its distal end 104 for connecting to a corresponding threaded portion of the container (18, see FIG. 4A) of the consumable (e.g., the cell delivery consumable 5*a*, see FIG. 4A). The threaded portion 107 is formed on the upper housing portion 102*a*. As will be clear to the skilled person, the housing 102 may be provided without the threaded portion 107, and instead be provided with another suitable connection mechanism for connecting to a portion of the container (18, see FIG. 4A).

The connector 19 also includes a connector portion at its proximal end 106 for connecting to the bioreactor (4, see FIG. 3), in particular, a connector interface (21, see FIG. 4B) of the bioreactor 4. The connector portion may be a groove 138, as illustrated in FIG. 5, configured to receive one or more protrusions or legs on the bioreactor. Alternatively, the connector 19 may comprise a threaded portion or other connector portion for connecting to the bioreactor.

In this embodiment, the connector 19 includes a first septum seal 108 disposed at the distal end 104 of the housing 102, and a second septum seal 110 disposed at the proximal end 106 of the housing 102. The first septum seal 108 includes a substantially planar, i.e., flat, pierceable surface facing outwardly at the distal end 104. The second septum seal 110 includes a generally annular portion, extending outwardly at the proximal end 106, enclosing a substantially planar, i.e., flat, pierceable surface facing outwardly at the proximal end 106. The housing 102 further includes a hollow needle 112 that is biasedly mounted within the housing 102. The hollow needle 112 is generally coaxially aligned with the longitudinal axis. The hollow needle 112 includes a first end 114, facing the first septum seal 108, and a second end 116, facing the second septum seal 110. The first end 114 is configured to be able to pierce the first septum seal 108, in use, and the second end 116 is configured to be able to pierce the second septum seal 110, in use. The first septum seal 108, the second septum seal 110, or both the first and second septum seal 108, 110 may optionally be provided with a removable aseptic paper seal 111.

The hollow needle 112 is mounted within the housing 102 through a collar 118 that is spring-biased by a first helical spring 120 and a second helical spring 122. In other embodiments, the hollow needle 112 may be mounted in another suitable manner, for example, the hollow needle 112 may be statically mounted, i.e., such that it does not move, and the housing 102 may be moveable about the hollow needle 112. The first spring 120 acts between the distal end 104 of the housing 102 and the collar 118. The second spring 122 acts between the proximal end 106 of the housing 102 and the collar 118. In this way, the first spring 120 provides a first biasing force to the hollow needle 112, via the collar 118, in a direction toward the proximal end 106 of the housing 102, and the second spring 122 provides a second biasing force to the hollow needle 112, via the collar 118, in a direction toward the distal end 104 of the housing 102.

The connector 19 further includes an actuating mechanism for causing the hollow needle 112 to pierce the septum seals 108, 110. By piercing the first and second septum seals 108, 110 the hollow needle 112 creates a fluid path between the distal end 104 and the proximal end 106 of the connector 19, and so during use creates a fluid connection between the container 18 of the consumable (e.g., the cell delivery consumable 5*a* or media delivery consumable 5*c*, see FIG. 1) and the container 12 of the bioreactor 4, as shown in FIG. 4B.

In the example illustrated in FIG. 5 the actuating mechanism includes an outer sleeve 134 that is arranged to collapse the upper housing portion 102*a* with respect to the lower housing portion 102*b*. The outer sleeve 134 is rotatable with respect to the housing 102 about the central longitudinal axis of the housing 102. For example, one of the outer sleeve 134 and the housing 102 may include a helical groove, and the other of the outer sleeve 134 and housing 102 may include a protrusion that engages the groove such that when the upper housing portion 102*a* collapses with respect to the lower housing portion 102*b* the outer sleeve 134 is rotated.

When the connector 19 is attached to the container (18, see FIG. 4A), in particular, via the threaded portion 107, the first septum seal 108 seals the end of the container (18, see FIG. 4A). The proximal end 106 of the connector 19 is then attached to the connector interface (21, see FIG. 4B), for example, by a clipping mechanism, a sliding mechanism, a threaded connection, or clamping. In this position, actuation of the actuating mechanism, in particular, rotation of the outer sleeve 134, causes the upper housing portion 102*a* to collapse with respect to the lower housing portion 102*b* and the hollow needle 112 pierces the first septum seal 108 and the second septum seal 110 and creates a fluid connection through the connector 19, between the container (18, see FIG. 4A) and the bioreactor (4, see FIG. 4B).

Accordingly, the connector 19 initially provides a sealing closure for the container (18, see FIG. 4A), and the fluid connection is formed entirely within the connector 19, which advantageously maintains a sterile environment.

Once the fluid has been transferred from the consumable to the bioreactor (4, see FIG. 4B) (or vice versa) through the hollow needle 112, the actuation mechanism can be reversed so that the needle withdraws from the first septum seal 108 and optionally also the second septum seal 110. The first and/or second septum seal 108, 110 reseal on withdrawal of the hollow needle 112. The connector 19, and the container (18, see FIG. 4A), can then be detached from the bioreactor (4, see FIG. 4B).

In examples, an end of the container 18 of the consumable 5*a*, 5*b* illustrated in FIG. 4A comprises a plug seal, for example, a septum seal, so that the container 18 is sealed before the connector 19 is connected. The plug seal of the container 18 can be pierced by the hollow needle 112.

In examples, the connector interface 21 of the bioreactor 4 illustrated in FIGS. 3 and 4B comprises a further septum seal that is pierced by the hollow needle 112 in use. Accordingly, when the connector 19 is detached the bioreactor 4 remains sealed.

Figure 6:
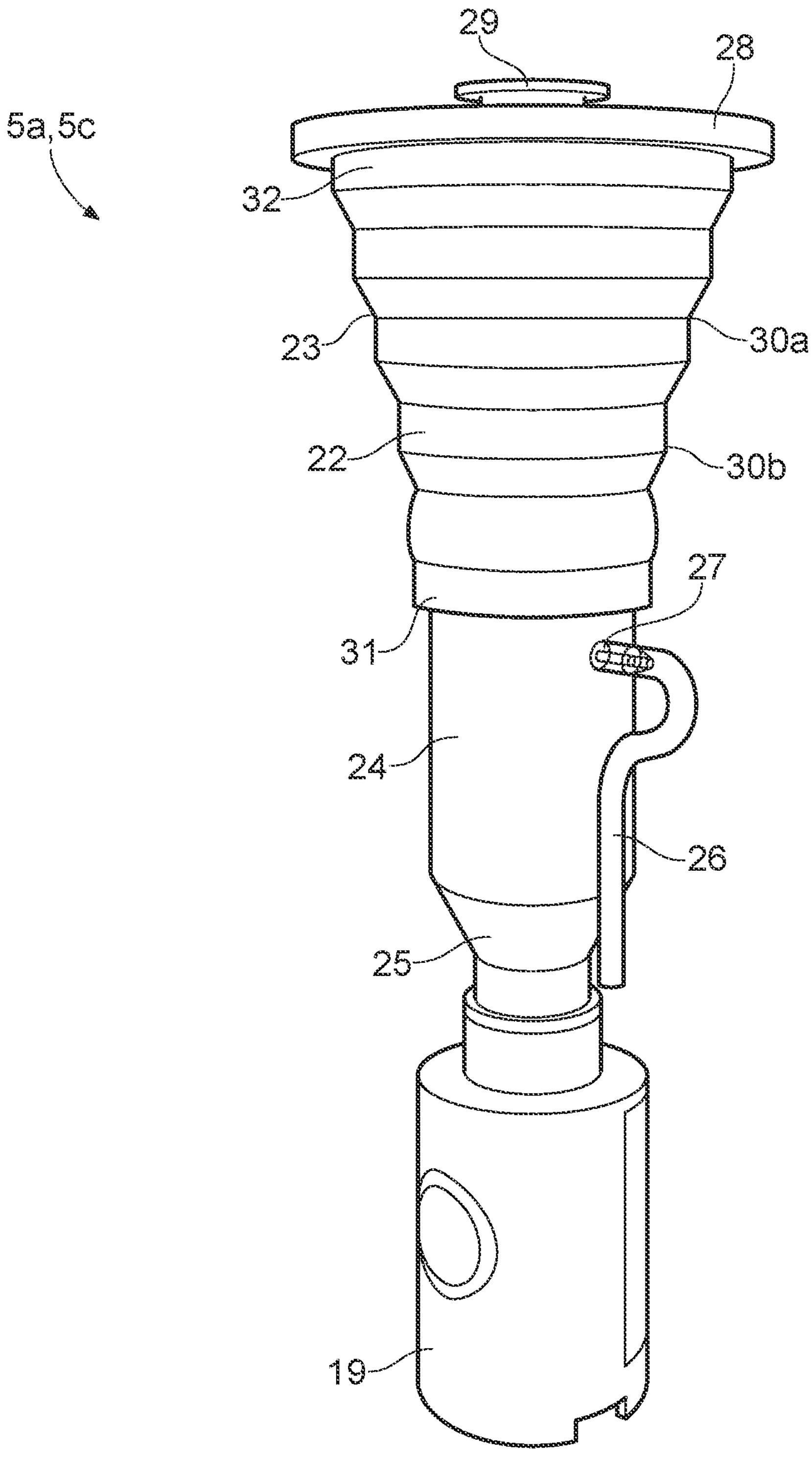
FIG. 6 shows an example fluid delivery consumable.

FIGS. 6 to 8B illustrate a first example delivery consumable 5*a*, 5*c*, for example, a cell delivery consumable 5*a* or a media delivery consumable 5*c*. As shown in FIG. 6, the delivery consumable 5*a*, 5*c* comprises a collapsible portion 22, a connector 19, and an intermediate portion 24. The intermediate portion 24 is arranged between the collapsible portion 22 and the connector 19.

The connector 19, described with reference to FIG. 5, may be attached to the intermediate portion 24, for example, via a threaded connection (see threaded portion 107 in FIG. 5). In other examples, the connector 19 may be integral with the intermediate portion 24.

The connector 19 is connectable to the bioreactor (4, see FIG. 3), in particular, to the connector interface (21, see FIG. 3) of the bioreactor 4, as previously described. As described with reference to FIG. 5, after the connector 19 has been attached to the bioreactor 4 it can be actuated to create a fluid connection between the delivery consumable 5*a*, 5*c* and the bioreactor 4. After the fluid connection is formed by the connector 19 the collapsible portion 22 can be collapsed to urge the fluid into the bioreactor 4.

In other examples the connector of the delivery consumable 5*a*, 5*c* may comprise an openable valve, a breakable seal, or other sealing mechanism that initially seals the delivery consumable 5*a*, 5*c* and is openable once the connector is connected to the bioreactor to provide a fluid connection between the delivery consumable 5*a*, 5*c* and the bioreactor.

The fluid provided to the delivery consumable 5*a*, 5*c* may be received in the intermediate portion 24. In examples, all of the fluid provided to the delivery consumable 5*a*, 5*b* is received in the intermediate portion 24. This is particularly advantageous where the fluid is a cell suspension and the delivery consumable is a cell delivery consumable 5*a*, as the cells are valuable and delicate and it may be beneficial to prevent them from contacting the collapsible portion 22.

As shown in FIG. 6, the intermediate portion 24 comprises a container portion and a funnel portion 25. The intermediate portion 24 defines an internal volume in which the fluid is held. The intermediate portion 24 may be transparent so that a user can see the fluid in the delivery consumables 5*a*, 5*c*, and can see that the fluid has been transferred to the bioreactor after use. The intermediate portion 24 may comprise volume markings to indicate the volume of fluid in the delivery consumable 5*a*, 5*c*.

The connector 19 is disposed at an end of the intermediate portion 24, and the connector 19 may comprise a seal that extends across an end of the intermediate portion 24 to seal it. For example, the connector 19 may comprise a plug that plugs an end of the intermediate portion 24. The plug may include a septum seal for creating a fluid connection through the plug during use. As shown in FIG. 6, the connector 19 is arranged at the end of the funnel portion 25 of the intermediate portion 24.

The collapsible portion 22 has a collapsible wall 23 that may be described as a bellows wall. The collapsible wall 23 has a series of alternating inward folds 30*a* an outward folds 30*b* that allow the collapsible wall 23 to collapse. A first end 31 of the collapsible wall 23 is attached to the intermediate portion 24, and a second end 32 of the collapsible wall 23, opposite to the first end 31, is provided with a cap 28. Accordingly, the internal volume of the collapsible portion 22 is sealed and in communication with the internal volume of the intermediate portion 24.

The first end 31 of the collapsible wall 23 can be attached to the intermediate portion 24 by clamping, adhering, or welding. In other examples, the first end 31 of the collapsible wall 23 and the intermediate portion 24 are integrally molded, for example, overmolded, and formed as one component. The cap 28 can be attached to the second end 32 of the collapsible wall 23 by clamping, adhering, or welding.

In the example illustrated in FIG. 6 the collapsible wall 23 is frustoconical and the second end 32 is larger than the first end 31. That is, the first end 31 that is connected to the intermediate portion 24 is smaller than the second end 32. Accordingly, when the delivery consumable 5*a*, 5*c* is substantially vertical, with the connector 19 at a lower position, the collapsible portion 22 is an inverted frustoconical form. However, in other examples the first end 31 may be larger than the second end 32, or the collapsible wall 23 may be cylindrical such that the first end 31 is the same size as the second end 32.

In the illustrated example the collapsible portion 22 has a generally circular cross-section. However, it will be appreciated that other cross-sectional shapes are possible, providing other frustoconical forms for the collapsible portion 22. For example, the collapsible portion 22 may comprise a square frustrum, or a pyramid frustrum. In such examples, the collapsible wall 23 may comprise straight sides and corners, and the corners may comprise deformable portions or weakened portion to allow the collapsible wall 23 to collapse.

In examples, the cap 28 may comprise an engaging feature 29 that is engageable by another part of the cell processing system (1, see FIG. 1), in particular, an actuator in the cell processing housing (2, see FIG. 1). The actuator may engage the engaging feature 29, for example, to compress and/or expand the collapsible portion 22.

In examples, the cap 28 may include a septum seal permitting filling of the cell suspension through the septum seal by a needle and syringe.

Additionally or alternatively, as shown in FIG. 6, the intermediate portion 24 may include a feed tube 26. The feed tube 26 is in fluid communication with the internal volume of the intermediate portion 24 via an opening in the intermediate portion 24. In this example a spigot 27 is formed on the intermediate portion 24 for attachment of the feed tube 26. The feed tube 26 can be used to feed a fluid into the delivery consumable 5*a*, 5*c*, in particular, into the intermediate portion 24. After filling, the feed tube 26 can be detached or sealed off, for example, plugged or welded shut. Any part of the feed tube 26 remaining attached to the delivery consumable 5*a*, 5*b* can be clipped to the intermediate portion 24 as illustrated. The feed tube 26 may be particularly advantageous for a cell delivery consumable 5*a* as the cell suspension can be provided to the intermediate portion 24 via the feed tube 26 directly from an upstream source of the cells, for example, a bag.

The fluid can be delivered to the feed tube 26 by a gravity fed system, for example, from a bag. Alternatively, the fluid can be delivered to the feed tube 26 by a pump, for example, a peristaltic pump.

In other examples the delivery consumable 5*a*, 5*c* may be filled with a fluid through the connector 19. For example, the connector 19 may be connected to a filling module, the hollow needle (112, see FIG. 5) may create a fluid connection to the internal volume of the delivery consumable 5*a*, 5*c*, and the filling module may transfer a fluid into the delivery consumable 5*a*, 5*c*.

During use, a fluid is provided to the delivery consumable 5*a*, 5*c*, in particular, the intermediate portion 24, via the feed tube 26 and/or septum seal and/or via the connector 19. Before filling the collapsible portion 22 may be at least partially collapsed, and during filling the collapsible portion 22 may extend as the fluid displaces air (or other gas) within the delivery consumable 5*a*, 5*c*. In examples, the collapsible portion 22 may be partially or fully expanded before filling, so as to create a lower pressure within the delivery consumable 5*a*, 5*c* that draws the fluid into the delivery consumable 5*a*, 5*c*.

After filling the connector 19 is connected to the bioreactor (4, see FIG. 3), in particular, the connector interface (21, see FIG. 3) of the bioreactor 4. The collapsible portion 22 can then be collapsed, either manually or mechanically, to urge the fluid through the connector 19 and into the bioreactor 4. The delivery consumable 5*a*, 5*c* is generally vertically oriented during transfer so that the connector 19 is at a lower end and the collapsible portion 22 is above the connector 19. In this orientation, collapsing the collapsible portion 22 creates a pressure above the fluid that urges the fluid through the fluid connection formed by the connector 19.

Figures 7A, 7B:
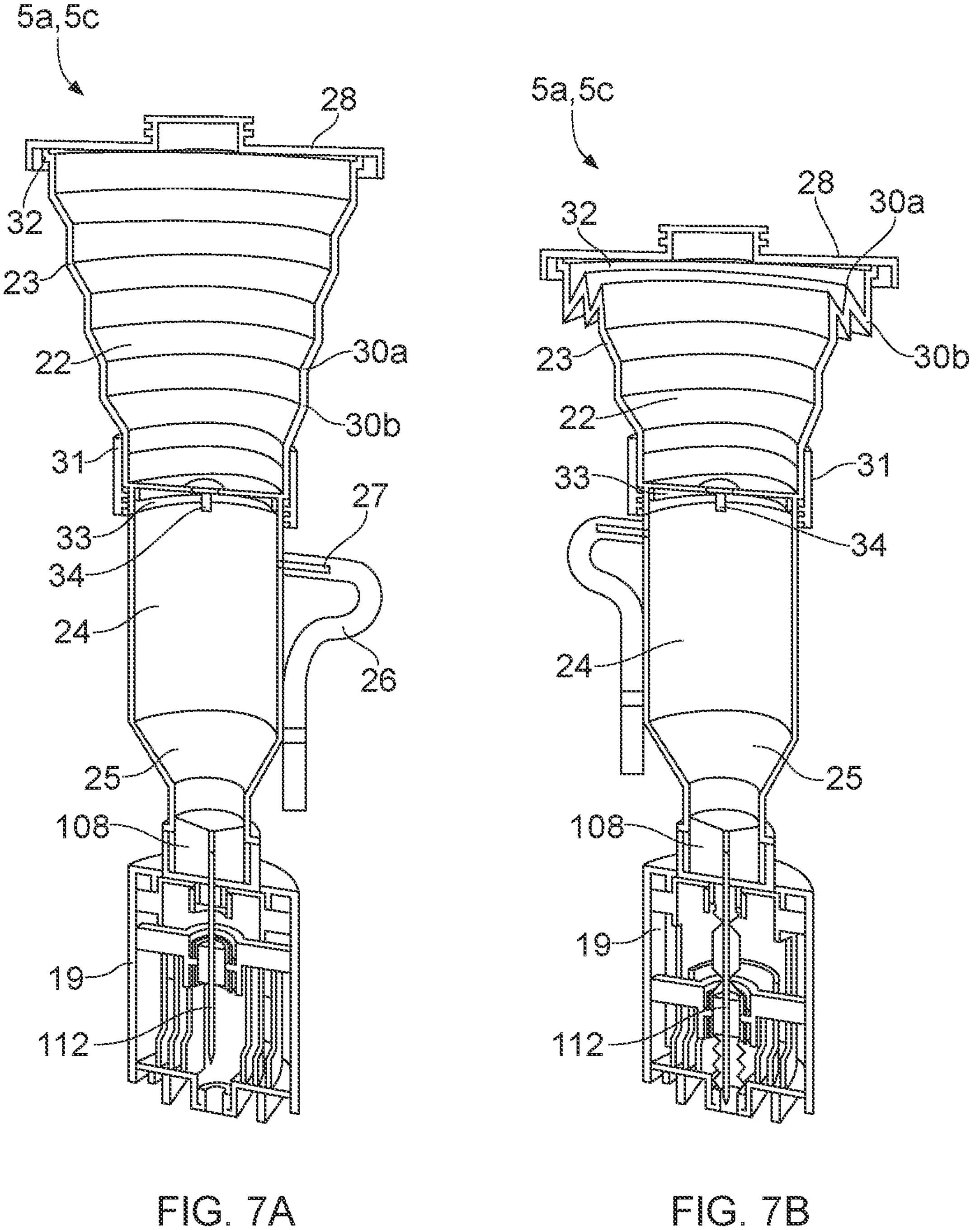
FIGS. 7A and 7B show cross-sectional views of the fluid delivery consumable of FIG. 6.

FIGS. 7A and 7B show cross-sections of the delivery consumable 5*a*, 5*c* of FIG. 6. In particular, the delivery consumable 5*a*, 5*c* of FIGS. 6A and 6B includes a collapsible portion 22, an intermediate portion 24, and a connector 19.

FIG. 7A shows the delivery consumable 5*a*, 5*c* in a full state, prior to collapsing the collapsible portion 22. FIG. 7B shows the delivery consumable 5*a*, 5*c* after partially collapsing the collapsible portion 22. As shown in FIG. 7B, when the collapsible portion 22 is collapsed the collapsible wall 23 is folded about the inward and outward folds 30*a*, 30*b*, reducing the distance between the first end 31 and the second end 32 and therefore reducing the internal volume in the collapsible portion 22 and within the delivery consumable 5*a*, 5*c* as a whole.

As shown in FIGS. 7A and 7B, the delivery consumable 5*a*, 5*c* may also include a divider 33 arranged to separate the internal volumes of the collapsible portion 22 and the intermediate portion 24. The divider 33 includes a valve 34, such as two-way valve. The valve 34 permits passage of air (or other gas within the delivery consumable 5*a*, 5*c*) from the intermediate portion 24 to the collapsible portion 22 when the delivery consumable 5*a*, 5*c* is being filled with fluid, and permits passage of air (or other gas within the delivery consumable 5*a*, 5*c*) from the collapsible portion 22 to the intermediate portion 24 as the collapsible portion 22 is collapsed to transfer the fluid to the bioreactor. The divider 33 may act to prevent the fluid from moving from the intermediate portion 24 into the collapsible portion 22.

Additionally or alternatively, the divider 33, in particular, the valve 34, may restrict air flow through the valve in order to limit the rate at which the collapsible portion 22 can be collapsed, and therefore limit the pressure that can be applied to the fluid and limit the rate at which the fluid is transferred to the bioreactor. This may help to protect the cells or other delicate constituents of the fluid from damage caused by flowing too quickly through the needle connecting the delivery consumable 5*a*, 5*c* to the bioreactor.

Also shown in FIGS. 7A and 7B the first septum seal 108 of the connector 19 seals the end of the intermediate portion 24. As described with reference to FIG. 5, the connector 19 is actuatable to move a hollow needle 112 relative to the first septum seal 108 and to puncture first septum seal 108 to create a fluid connection across the first septum seal 108.

Figures 8A, 8B:
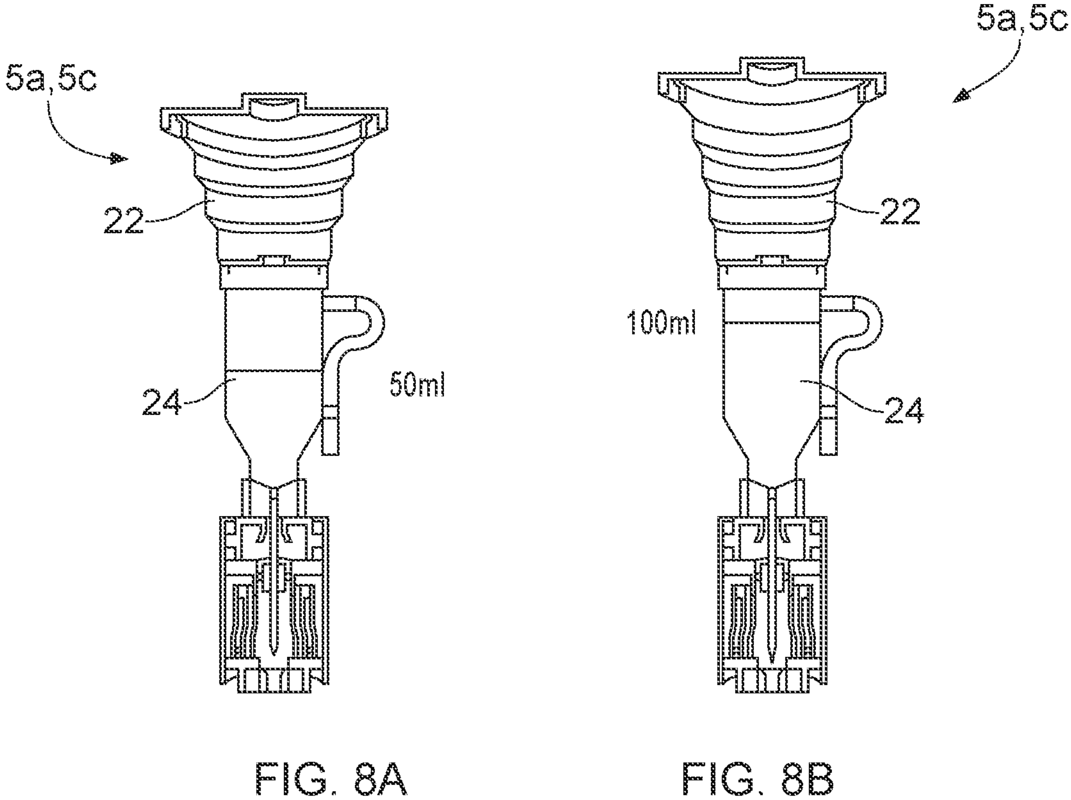
FIGS. 8A and 8B show example fluid delivery consumables with different volumes.

FIGS. 8A and 8B illustrate the delivery consumable 5*a*, 5*c* of FIGS. 6, 7A, and 7B with different volumes of fluid. In the example of FIG. 8A the delivery consumable 5*a*, 5*c* may hold about 50 ml of fluid, and in the example of FIG. 8B the delivery consumable 5*a*, 5*c* may hold about 100 ml of fluid. In examples, the 50 ml or 100 ml fluid is a cell suspension. The difference in volume may be accommodated by having different sized delivery consumables 5*a*, 5*c*, with different size intermediate portions 24 and collapsible portions 22. Alternatively, the difference may be accounted for within the volume of the same delivery consumable 5*a*, 5*c*, by only partially expanding the collapsible portion 22 when the amount of fluid is less than a maximum capacity.

Figure 9:
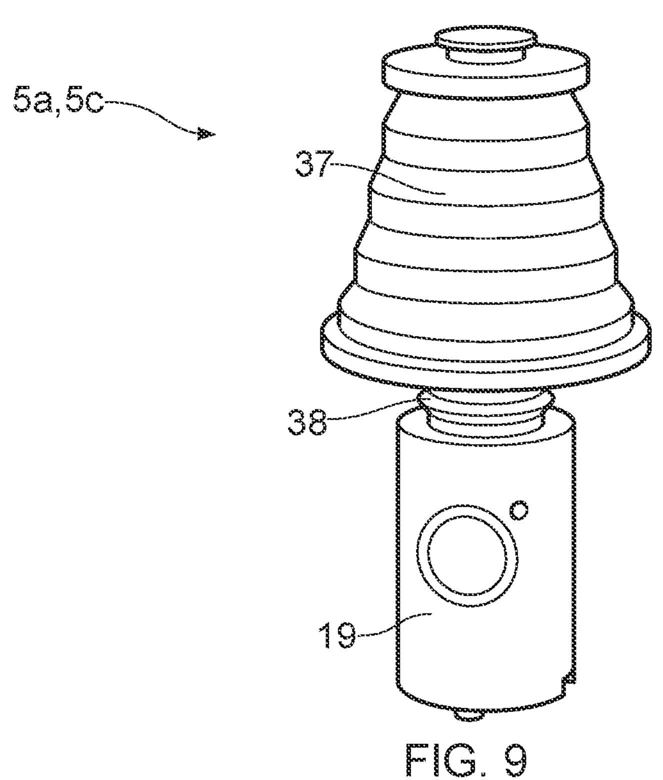
FIG. 9 shows a further example fluid delivery consumable.
Figure 10:
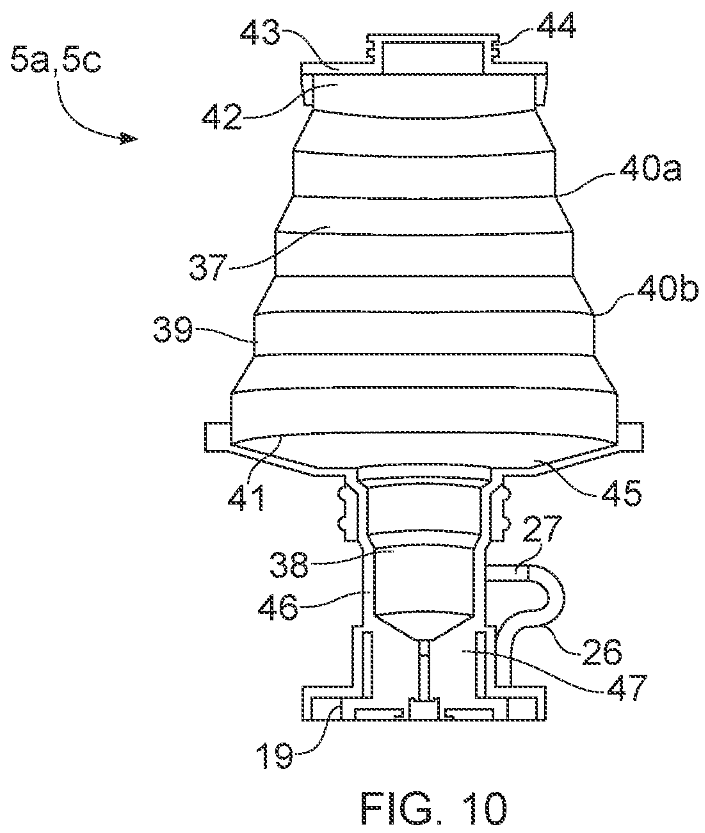
FIG. 10 shows a cross-section of the fluid delivery consumable of FIG. 9.
Figure 11:
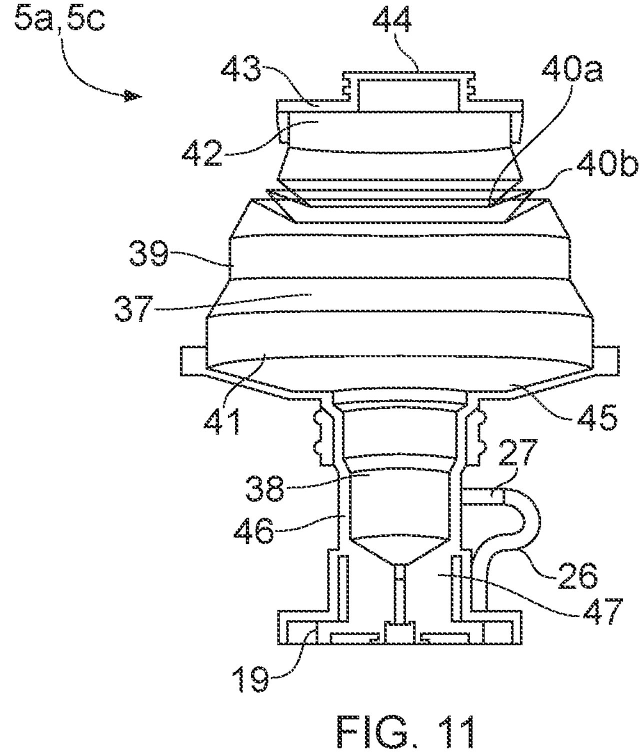
FIG. 11 shows a cross-section of the fluid delivery consumable of FIG. 9 in a partially collapsed state.

FIGS. 9 to 11 illustrate another example of the delivery consumable 5*a*, 5*c*. In this example, as shown in FIG. 9, the delivery consumable 5*a*, 5*c* comprises a connector 19, a collapsible portion 37, and an intermediate portion 38 between the collapsible portion 37 and the connector 19.

The connector 19 may be the same connector 19 as described with reference to the examples of FIGS. 4A to 5. In particular, the connector 19 is connectable to the bioreactor (4, see FIG. 3), in particular, the connector interface (21, see FIG. 3) of the bioreactor 4. The connector 19 may include a needle that is actuatable to puncture a seal of the delivery consumable 5*a*, 5*c* and create a fluid connection between the delivery consumable 5*a*, 5*c* and the bioreactor 4.

In other examples, the connector of the delivery consumable 5*a*, 5*c* may comprise an openable valve, a breakable seal, or other sealing mechanism that initially seals the delivery consumable 5*a*, 5*c* and is openable once the connector is connected to the bioreactor to provide a fluid connection between the delivery consumable 5*a*, 5*c* and the bioreactor.

In this example, the fluid, for example, a cell suspension, is held within the intermediate portion 38 and within the collapsible portion 37. During use compression of the collapsible portion 37 urges the fluid through the fluid connection provided by the connector 19.

In FIG. 10 the connector 19 is only partially shown. As illustrated in FIG. 10, the collapsible portion 37 is formed of a collapsible wall 39 having a series of alternating inward folds 40*a* and outward folds 40*b*. The collapsible wall 39 may be called a bellows wall.

In this example, a first end 41 of the collapsible wall 39 is attached to the intermediate portion 38, and a second end 42 of the collapsible wall 39 is disposed opposite to the first end 41. A cap 43 closes the second end 42. As with the previous examples, the cap 43 may include an engaging feature 44 that is engageable by another part of the cell processing system (1, see FIG. 1), in particular, an actuator in the cell processing housing (2, see FIG. 1).

The first end 41 of the collapsible wall 39 can be attached to the intermediate portion 38 by clamping, adhering, or welding. In other examples, the first end 41 of the collapsible wall 39 and the intermediate portion 38 are integrally molded, for example, overmolded, and formed as one component. The cap 43 can be attached to the second end 42 of the collapsible wall 39 by clamping, adhering, or welding.

In this example, the first end 41 of the collapsible wall 39 is larger than the second end 42 of the collapsible wall 39, and so the collapsible portion 37 is frustoconical. The frustoconical collapsible portion 37 tapers away from the intermediate portion 38. That is, the frustoconical collapsible portion 37 has a larger cross-section at the intermediate portion 38 than at the second end 42. As shown in FIG. 11, the frustoconical collapsible portion 37 with the larger (first) end 41 being attached to the intermediate portion 38 ensures that fluid cannot be trapped within the folds 40*a*, 40*b* of the collapsible wall 39 when the collapsible wall 39 is collapsed. In particular, the inward and outward folds 40*a*, 40*b* cause the collapsed part the collapsible wall 39 to be angled downwards, toward the intermediate portion 38, thereby preventing fluid from becoming trapped between the folds 40*a*, 40*b*. Accordingly, even though the frustoconical collapsible portion 37 is arranged like an inverted funnel, advantageously fluid is less liable to be retained in the folds of the collapsible wall 39. This is particularly advantageous for a cell delivery consumable 5*a* as the cells are valuable and delicate and it is preferable to transfer as many cells as possible into the bioreactor and retain as few as possible in the cell delivery consumable 5*a*.

As shown in FIG. 10, the intermediate portion 38 includes a funnel portion 45 attached to the first end 41 of the collapsible portion 37. The funnel portion 45 narrows in a direction away from the collapsible portion 37 and the tubular portion 46 extends to the connector 19. As with the previous examples, a plug seal 47 may seal the end of the intermediate portion 38, in particular, the tubular portion 46. The plug seal 47 can be punctured by the hollow needle (112, see FIG. 5) of the connector 19 as previously described.

As shown in FIG. 10, the intermediate portion 38 also includes a feed tube 26 and spigot 27 attaching the feed tube 26 to the intermediate portion 38. The feed tube 26 can be used to fill the delivery consumable 5*a*, 5*c* with a fluid, for example, a cell suspension or cell culturing media, and can then be detached or sealed.

Figure 12A:
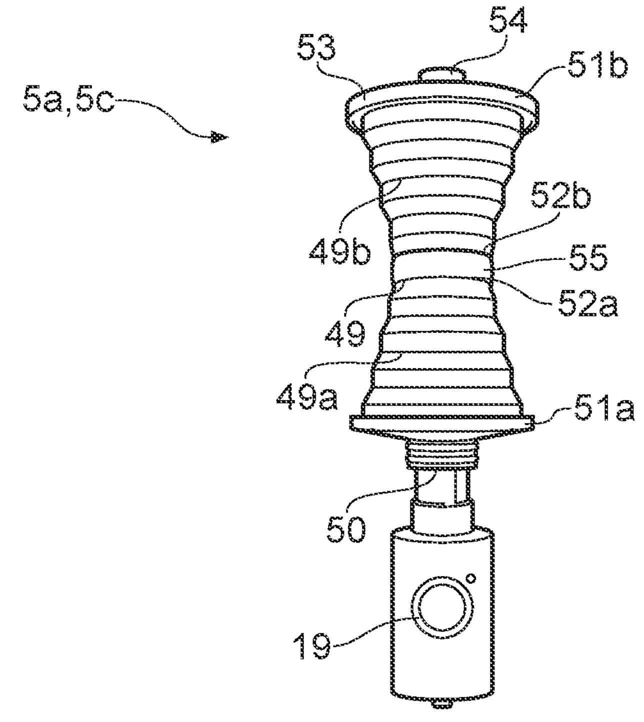
FIGS. 12A and 12B illustrate a further example fluid delivery consumable.
Figure 12B:
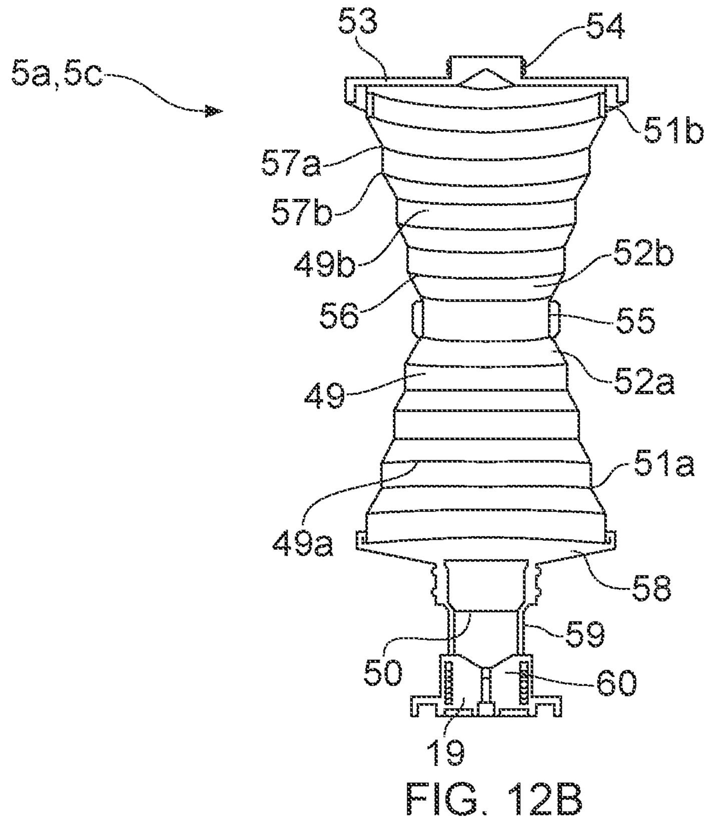

FIGS. 12A and 12B illustrate another example of the delivery consumable 5*a*, 5*c*. In this example, as shown in FIG. 12A, the delivery consumable 5*a*, 5*c* comprises a connector 19, a collapsible portion 49, and an intermediate portion 50 between the collapsible portion 49 and the connector 19. In FIG. 12B the connector 19 is only partially shown.

The connector 19 may be the same connector 19 as described with reference to the examples of FIGS. 4A to 5. In particular, the connector 19 is connectable to the bioreactor (4, see FIG. 3), in particular, the connector interface (21, see FIG. 3) of the bioreactor 4. The connector 19 may include a needle that is actuatable to puncture a seal of the delivery consumable 5*a*, 5*c* and create a fluid connection between the delivery consumable 5*a*, 5*c* and the bioreactor 4.

In other examples, the connector of the delivery consumable 5*a*, 5*c* may comprise an openable valve, a breakable seal, or other sealing mechanism that initially seals the delivery consumable 5*a*, 5*c* and is openable once the connector is connected to the bioreactor to provide a fluid connection between the delivery consumable 5*a*, 5*c* and the bioreactor.

In this example, the fluid, for example, a cell suspension, is held within the intermediate portion 50 and within the collapsible portion 49. During use compression of the collapsible portion 49 urges the fluid through the fluid connection provided by the connector 19.

In the example of FIGS. 12A and 12B, the collapsible portion 49 comprises a first collapsible portion 49*a* and a second collapsible portion 49*b*. Each of the first and second collapsible portions 49*a*, 49*b* has a frustoconical form. Each of the first and second collapsible portions 49*a*, 49*b* has a first end 51*a*, 51*b* and a second end 52*a*, 52*b*, the first ends 51*a*, 51*b* being larger than the second ends 52*a*, 52*b*. The first and second collapsible portions 49*a*, 49*b* are joined end-to-end such that they define a single internal volume and collapse in the same direction. In the illustrated example the second ends 52*a*, 52*b* (i.e., the smaller ends) are joined to each other. The first end 51*a* of the first collapsible portion 49*a* is attached to the intermediate portion 50. The first end 51*b* of the second collapsible portion 49*b* is provided with a cap 53. Accordingly, from the intermediate portion 50 the collapsible portion 49 tapers inwards to a narrower waist 55 and then tapers outwards to the first end 51*b* of the second collapsible portion 49*b*.

The first end 51*a* of the first collapsible portion 49*a* can be attached to the intermediate portion 50 by clamping, adhering, or welding. In other examples, the first end 51*a* of the first collapsible portion 49*a* and the intermediate portion 50 are integrally molded, for example, overmolded, and formed as one component. The cap 53 can be attached to the first end 51*b* of the second collapsible portion 49*b* by clamping, adhering, or welding.

As with the previous examples, the cap 53 may include an engaging feature 54 that is engageable by another part of the cell processing system (1, see FIG. 1), in particular, an actuator in the cell processing housing (2, see FIG. 1).

As illustrated in FIG. 12B, the collapsible portion 49 is formed of a collapsible wall 56 having a series of alternating inward folds 57*a* and outward folds 57*b*. The collapsible wall 56 may be called a bellows wall.

As shown in FIG. 12B, the intermediate portion 50 includes a funnel portion 58 attached to the first end 51*a* of the first collapsible portion 49*a*. The funnel portion 58 narrows in a direction away from the collapsible portion 49 and a tubular portion 59 extends to the connector 19. As with the previous examples, a plug seal 60, for example, a septum seal, may seal the end of the intermediate portion 50, in particular, the tubular portion 59. The plug seal 60 can be punctured by the hollow needle (112, see FIG. 5) of the connector 19 as previously described.

As with previous examples, the intermediate portion 50 may also include a feed tube and spigot attaching the feed tube to the intermediate portion 50. The feed tube can be used to fill the delivery consumable 5*a*, 5*c* with a fluid, for example, a cell suspension or cell culturing media, and can then be detached or sealed.

In examples, referring to all of the examples described above, the collapsible wall 23, 39 of the collapsible portion 22, 37 of the delivery consumable 5*a*, 5*c* may be made from silicone. In other examples the collapsible wall 23, 39 of the collapsible portion 22, 37 of the delivery consumable 5*a*, 5*c* may be made from another polymer, for example, polyethylene (PE), or a thermoplastic elastomer (TPE) such as polypropylene. Advantageously, the material of the collapsible wall 23, 39 may have a low elasticity or return force so that the collapsible wall 23, 39 retains its collapsed state after being collapsed. The collapsible wall 23, 39 may have an external or internal coating to reduce permeability, particularly gas permeability.

The various examples of delivery consumables 5*a*, 5*c* described above have been described in relation to delivering a fluid to the bioreactor (4, see FIG. 3), in particular, a cell suspension and/or a cell culturing media. However, it will be appreciated that the delivery consumables 5*a*, 5*c* may additionally or alternatively be used for delivering other fluid materials or media to the bioreactor (4, see FIG. 3).

Figure 13A:
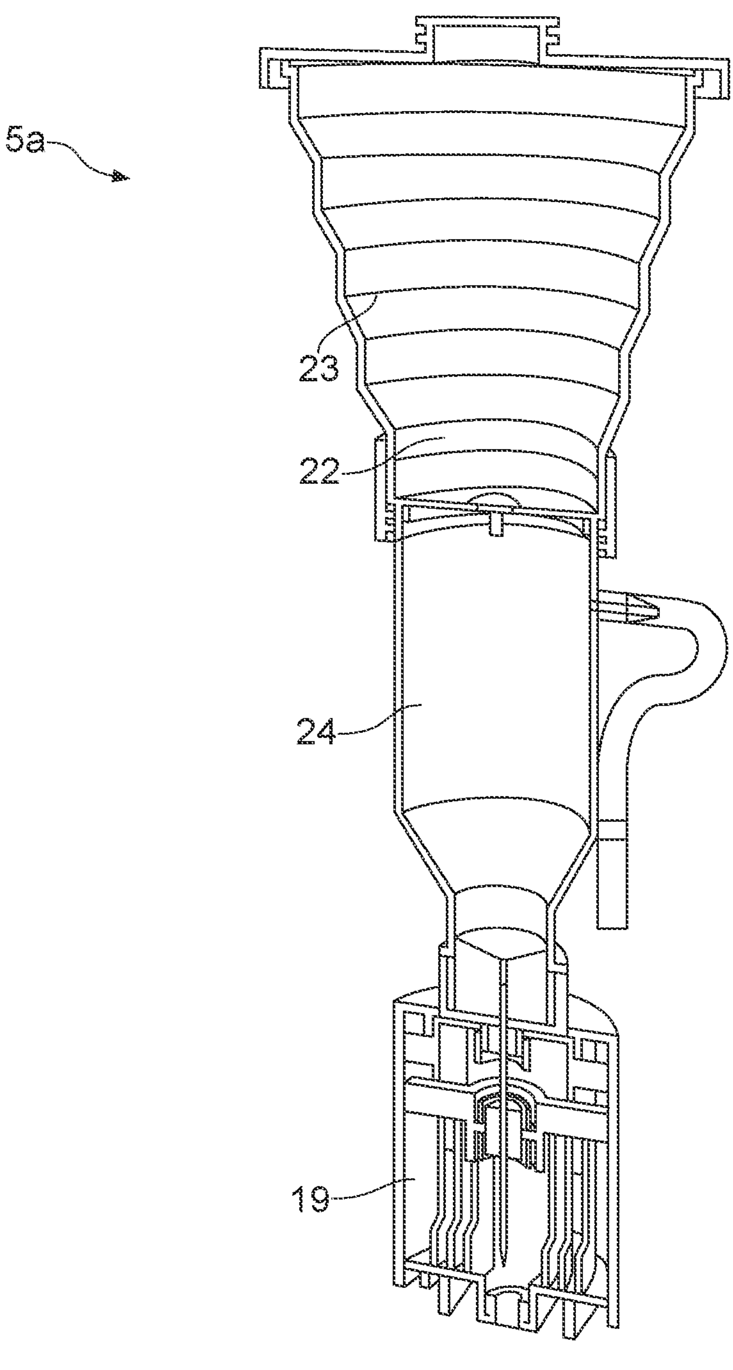
FIGS. 13A to 13E illustrate a method of delivering a fluid to the bioreactor using a fluid delivery consumable.
Figure 13B:
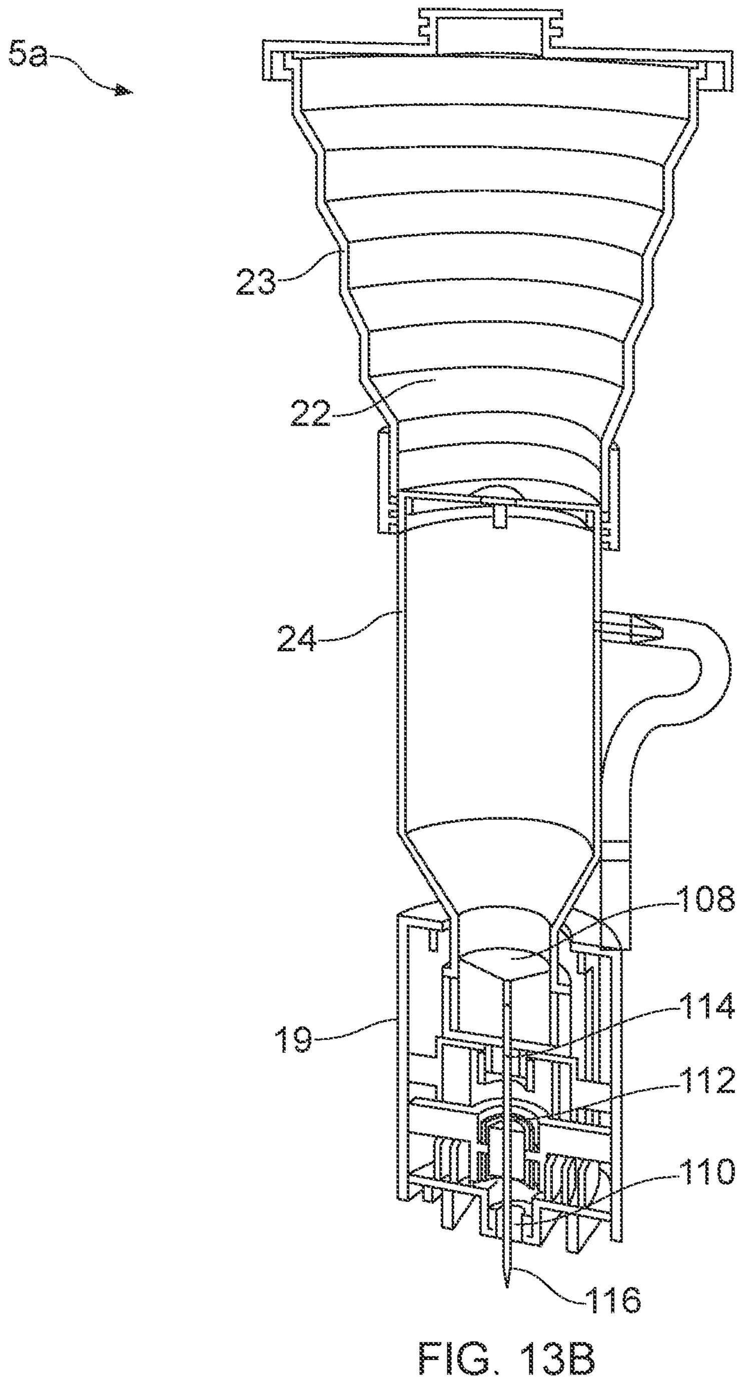
Figure 13C:
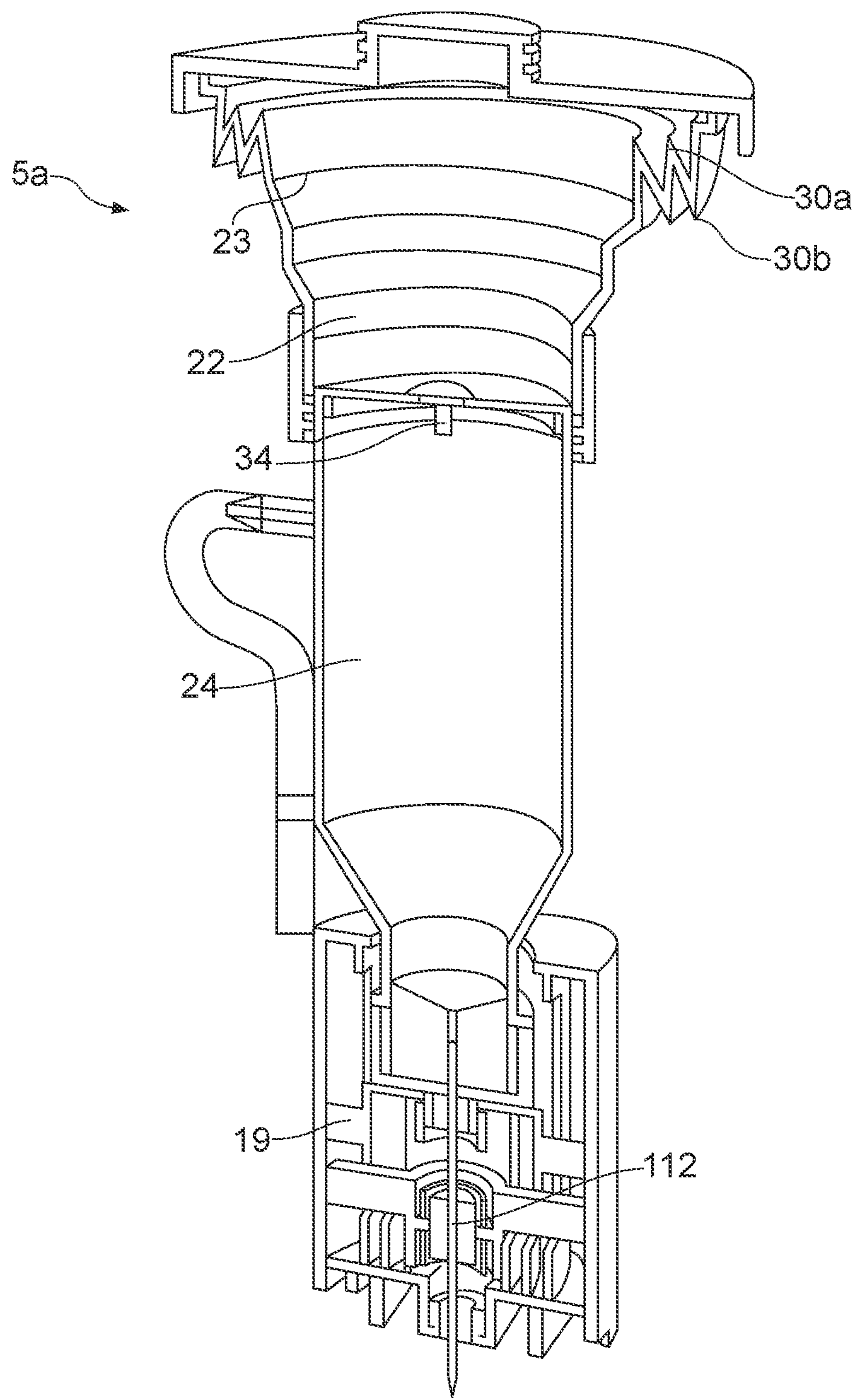
Figure 13D:
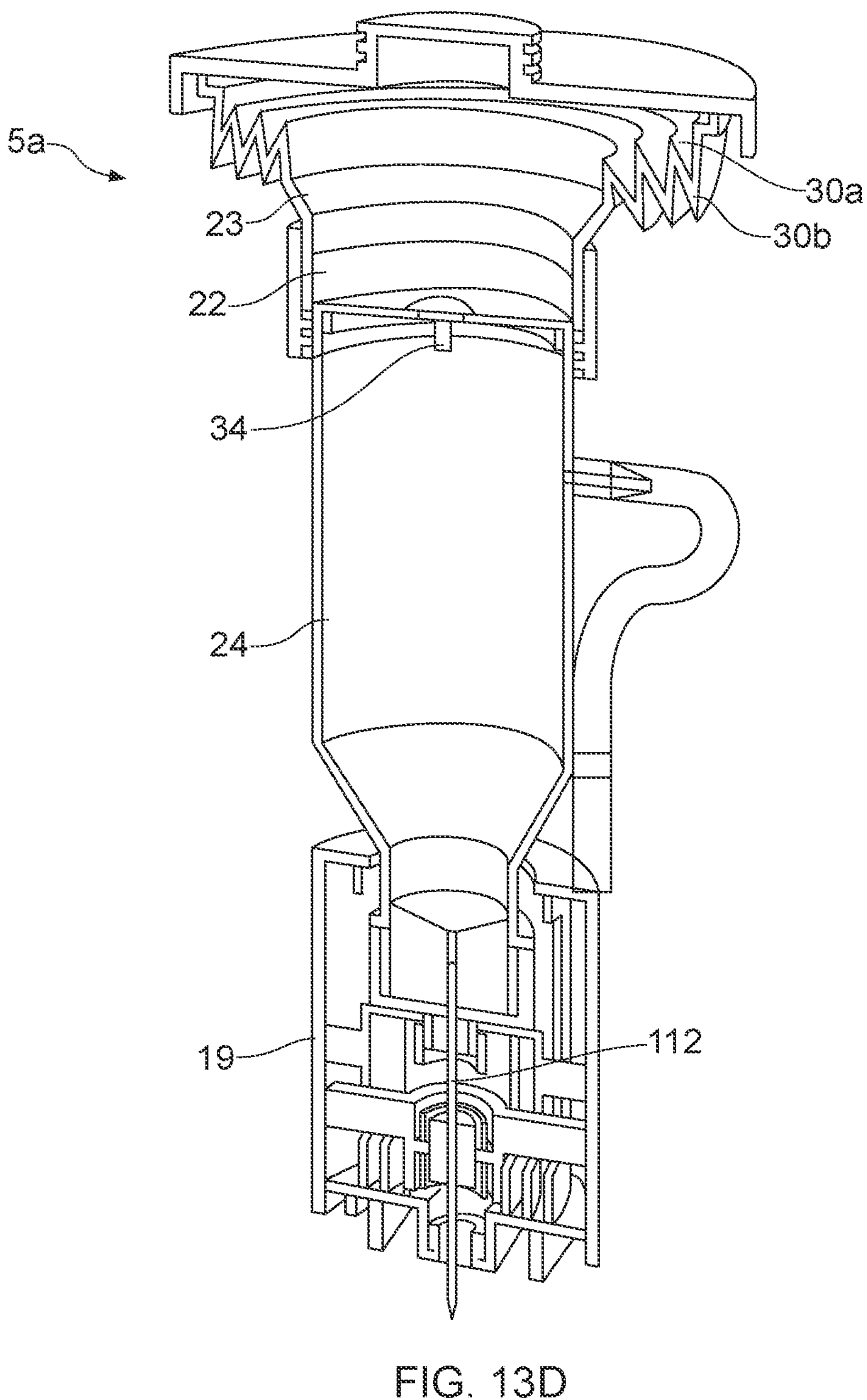
Figure 13E:
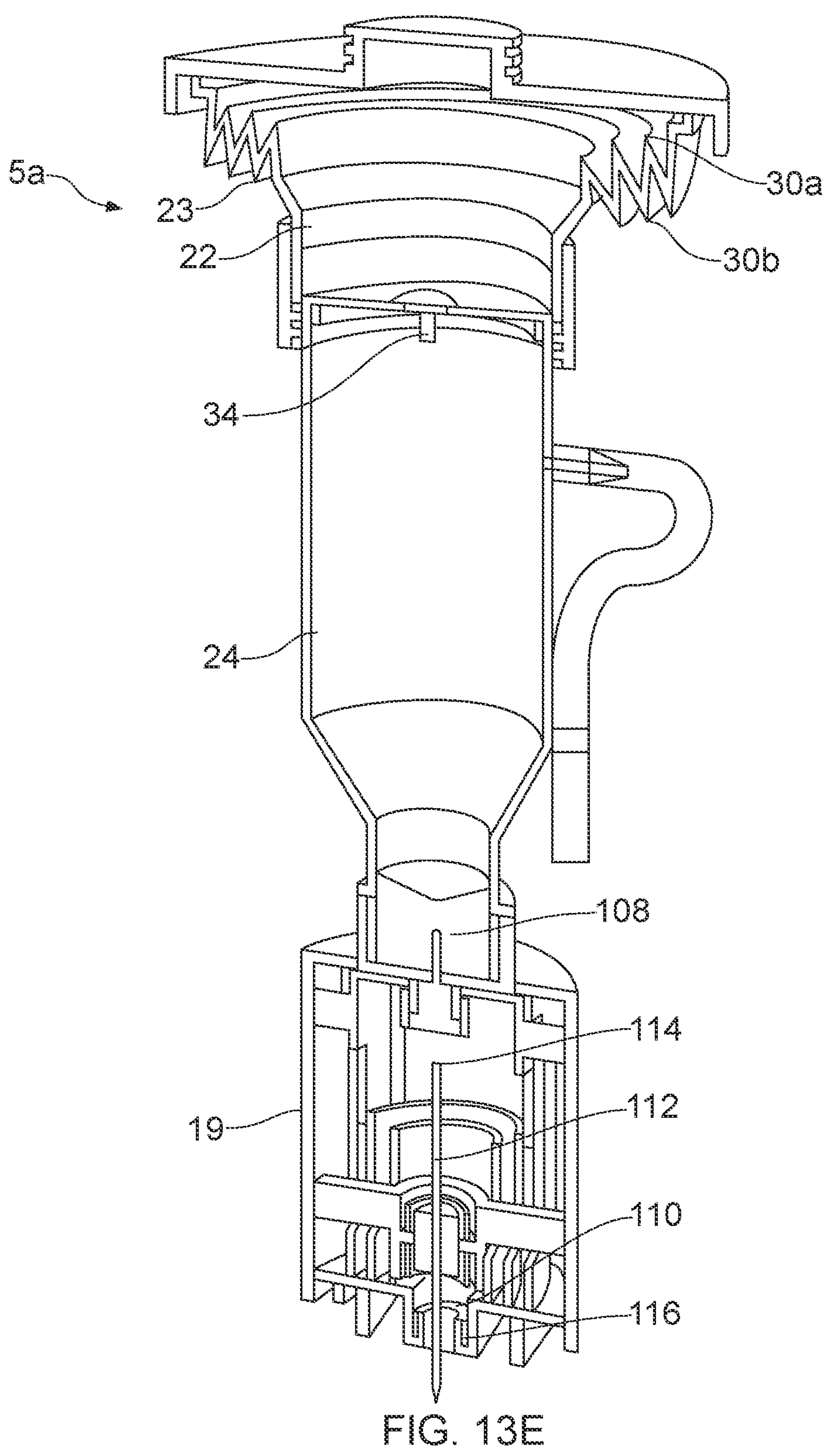

FIGS. 13A to 13E illustrate use of the delivery consumable 5*a*, 5*c* for delivering a fluid to a bioreactor (4, see FIG. 3). FIGS. 13A and 13E illustrate the process using the delivery consumable 5*a*, 5*c* of FIGS. 6 to 7B, but it will be appreciated that the same process applies for the delivery consumable 5*a*, 5*c* of FIGS. 9 to 11, and the delivery consumable of FIGS. 12A and 12B also.

As shown in FIG. 13A, when the delivery consumable 5*a*, 5*c* is full, with the fluid received in the intermediate portion 24, the collapsible portion 22 is in an extended state. The connector 19 is in a non-activated state, shown in FIG. 5, with a first end 114 of the needle 112 spaced from the first septum seal 108 of the connector, and a second end 116 of the needle 112 spaced from the second septum seal 110 of the connector 19. In this configuration the delivery consumable 5*a*, 5*c* can be transported and handled, and can be connected to the connector interface (21, see FIGS. 3 and 4B).

As shown in FIG. 13B, actuation of the connector 19 causes the connector 19 to collapse as described with reference to FIG. 5, such that the first end 114 of the hollow needle 112 pierces the first septum seal 108 and also any additional seal on the intermediate portion 24. In addition, the second end 116 of the hollow needle 112 pierces the second septum seal 110 of the connector 19 and also pierces any additional seal on the bioreactor (4, see FIG. 3). Accordingly, the needle 112 creates a fluid connection between the delivery consumable 5*a*, 5*c* and the bioreactor (4, see FIG. 4B).

FIGS. 13C and 13D shows compression of the collapsible portion 22, causing the volume within the delivery consumable 5*a*, 5*c* to be reduced and the fluid to be urged through the needle 112 and into the bioreactor (4, see FIG. 3). The collapsible wall 23 of the collapsible portion 22 concertinas as a result of the inward and outward folds 30*a*, 30*b*.

In the example of the delivery consumable 5*a*, 5*c* of FIGS. 6 to 7B, collapsing the collapsible portion 22 drives air through the valve 34 and urges the fluid through the hollow needle 112 and into the bioreactor (4, see FIG. 3). In the example of the delivery consumable 5*a*, 5*c* of FIGS. 9 to 12B, collapsing the collapsible portion 37 urges the fluid through the hollow needle 112 and into the bioreactor (4, see FIG. 3).

Once the desired volume of the fluid, for example, all of the fluid, has been transferred into the bioreactor (4, see FIG. 3) the connector 19 is disengaged so that the hollow needle 112 moves away from the first septum seal 108, as shown in FIG. 13E. Additionally, the hollow needle 112 may move away from the second septum seal 110. In this state the internal volume of the delivery consumable 5*a*, 5*b* is sealed from the connector 19, and the delivery consumable 5*a*, 5*c* and connector 19 can be disconnected from the bioreactor (4, see FIG. 3).

Throughout the description and claims of this specification, the words "comprise" and "contain" and variations of them mean "including but not limited to," and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

The invention claimed is:

1. A delivery consumable for delivering a fluid to a bioreactor, the delivery consumable comprising:

a container including:

a collapsible portion comprising a collapsible wall, wherein the collapsible wall comprises a plurality of inward folds and a plurality of outward folds arranged alternately between opposing ends of the collapsible wall; and an intermediate portion connected to the collapsible portion and being adapted to hold a fluid, and a connector adapted to connect the intermediate portion to the bioreactor, wherein the intermediate portion is arranged between the collapsible portion and the connector, wherein the collapsible portion comprises a frustrum-shaped collapsible wall, including at least a portion of the plurality of inward folds and outward folds, extending from a first end at the intermediate portion to a second end of the collapsible portion opposite to the first end, the first end being larger than the second end, and wherein the collapsible portion is adapted to collapse and urge the fluid from the intermediate portion, through the connector, and into the bioreactor.

2. The delivery consumable of claim 1, wherein the second end of the collapsible portion comprises a cap.

3. The delivery consumable of claim 1, wherein the collapsible portion further comprises a second collapsible wall including a second frustrum-shape extending from a second end to a first end, the first end being larger than the second end, and wherein the second end of the second collapsible wall is joined to the second end of the frustrum-shaped collapsible wall.

4. The delivery consumable of claim 1, wherein the collapsible portion is configured to hold at least a part of the fluid.

5. The delivery consumable of claim 1, further comprising a divider between the intermediate portion and the collapsible portion, the divider comprising a valve.

6. The delivery consumable of claim 5, wherein the intermediate portion is configured to hold the entire fluid provided to the delivery consumable.

7. The delivery consumable of claim 1, wherein a surface of the collapsible wall comprises a coating.

8. The delivery consumable of claim 1, wherein the connector comprises a seal arranged to seal an end of the intermediate portion, and wherein the connector is adapted to actuate to cause an action chosen from open the seal and break the seal to create a fluid connection from the intermediate portion through the connector.

9. The delivery consumable of claim 8, wherein the connector comprises a needle adapted to pierce the seal, and wherein the connector is adapted to actuate to cause the needle to pierce the seal.

10. The delivery consumable of claim 9, wherein the seal comprises a septum seal.

11. The delivery consumable of claim 1, further comprising a feed tube in fluid communication with the intermediate portion.

12. The delivery consumable of claim 11, wherein the intermediate portion comprises an external spigot for attachment of the feed tube.

13. The delivery consumable of claim 11, wherein the feed tube is adapted to close and seal the feed tube after a fluid has been added to the delivery consumable.

14. The delivery consumable of claim 1, wherein the delivery consumable is a cell delivery consumable and the fluid is a cell suspension.

15. The delivery consumable of claim 1, wherein the delivery consumable is a media delivery consumable and the fluid is a medium.

16. The delivery consumable of claim 1, comprising a fluid in the container.

17. A method of delivering a fluid to a bioreactor, the method comprising:

filling a delivery consumable with a fluid, the delivery consumable comprising: a collapsible portion comprising a collapsible wall, wherein the collapsible wall comprises a plurality of inward folds and a plurality of outward folds arranged alternately between opposing ends of the collapsible wall; and an intermediate portion connected to the collapsible portion and being adapted to hold a fluid, and a connector adapted to connect the intermediate portion to the bioreactor, wherein the intermediate portion is arranged between the collapsible portion and the connector, wherein the collapsible portion comprises a frustrum-shaped collapsible wall, including at least a portion of the plurality of inward folds and outward folds, extending from a first end at the intermediate portion to a second end of the collapsible portion opposite to the first end, the first end being larger than the second end, and wherein the collapsible portion is adapted to collapse and urge the fluid from the intermediate portion, through the connector, and into the bioreactor;

connecting the delivery consumable to the bioreactor via the connector of the delivery consumable; and at least partially collapsing the collapsible portion of the delivery consumable to transfer the fluid into the bioreactor.

* * * * *